(12) United States Patent  
Mann et al.

(10) Patent No.: US 6,622,048 B1  
(45) Date of Patent: Sep. 16, 2003

(54) IMPLANTABLE DEVICE PROGRAMMER

(75) Inventors: Carla M. Mann, Los Angeles, CA (US); Paul M. Meadows, La Crescenta, CA (US)

(73) Assignee: Advanced Bionics Corporation, Sylmar, CA (US)

(*) Notice: Subject to any disclaimer, the term of this patent is extended or adjusted under 35 U.S.C. 154(b) by 44 days.

(21) Appl. No.: 09/718,648

(22) Filed: Nov. 21, 2000

Related U.S. Application Data

(60) Provisional application No. 60/169,129, filed on Dec. 6, 1999.

(51) Int. Cl.$^7$ .................................................. A61N 1/02
(52) U.S. Cl. ........................................... 607/46; 607/59
(58) Field of Search ..................................... 607/46, 59

(56) References Cited

U.S. PATENT DOCUMENTS

| | | | | |
|---|---|---|---|---|
| 4,019,518 A | | 4/1977 | Maurer et al. ............... | 128/419 |
| 4,338,945 A | | 7/1982 | Kosugi et al. ............... | 128/421 |
| 4,793,353 A | * | 12/1988 | Borkan ........................ | 607/60 |
| 5,173,944 A | | 12/1992 | Begault ....................... | 381/17 |
| 5,330,515 A | | 7/1994 | Rutecki et al. ............... | 607/46 |
| 5,370,672 A | | 12/1994 | Fowler et al. ................ | 607/58 |
| 5,443,486 A | * | 8/1995 | Hrdlicka et al. .............. | 607/59 |
| 5,559,828 A | | 9/1996 | Armstrong et al. ......... | 375/200 |
| 5,643,330 A | | 7/1997 | Holsheimer et al. ......... | 607/46 |
| 5,683,432 A | | 11/1997 | Goedeke et al. ............. | 607/32 |
| 5,776,171 A | | 7/1998 | Peckham et al. ............. | 607/48 |
| 5,800,473 A | | 9/1998 | Faisandier ................... | 607/59 |
| 5,817,137 A | | 10/1998 | Kaemmerer ................. | 607/59 |
| 5,843,139 A | | 12/1998 | Goedeke et al. ............. | 607/32 |
| 5,893,883 A | * | 4/1999 | Torgerson et al. ........... | 607/59 |
| 5,913,882 A | | 6/1999 | King ............................ | 607/62 |
| 5,938,690 A | * | 8/1999 | Law et al. .................... | 607/46 |
| 5,954,758 A | | 9/1999 | Peckham et al. ............. | 607/48 |
| 6,052,624 A | * | 4/2000 | Mann .......................... | 607/46 |
| 6,308,102 B1 | * | 10/2001 | Sieracki et al. .............. | 607/59 |

FOREIGN PATENT DOCUMENTS

WO        0000251      6/2000

* cited by examiner

*Primary Examiner*—John Fox  
(74) *Attorney, Agent, or Firm*—Bryant R. Gold; Philip H. Lee

(57) ABSTRACT

A patient and/or a clinician may program an implant device, e.g., an implanted spinal cord stimulator (SCS), through the use of a programming computer, or clinician programmer, linked with the implant device so that the paresthesia resulting from an applied electrical stimulus pattern is adjusted or programmed so as to match the area of perceived pain or other need. Data is initially stored in the computer that relates to known information regarding the anatomical relationships between the spine and the body. The body is divided into dermatomes and/or subdivisions of dermatomes, and a representation of the body, including its dermatomes and/or subdivisions of dermatomes are displayed on the screen (or other display device) associated with the computer. The patient moves a cursor over the regions of the body displayed on the computer screen to select the region of pain, or a region of paresthesia, by a click of a mouse or the press of a button. The patient may select as many dermatomes or body segments/regions/subdivisions as necessary to communicate the area of pain or paresthesia to the computer. The computer uses the patient-provided information, as well as the pre-programmed data therein, to quickly zero in on an electrode combination and appropriate stimulus parameters that create a match (or as close of a match as is possible) between the pain region and the paresthesia region.

20 Claims, 12 Drawing Sheets

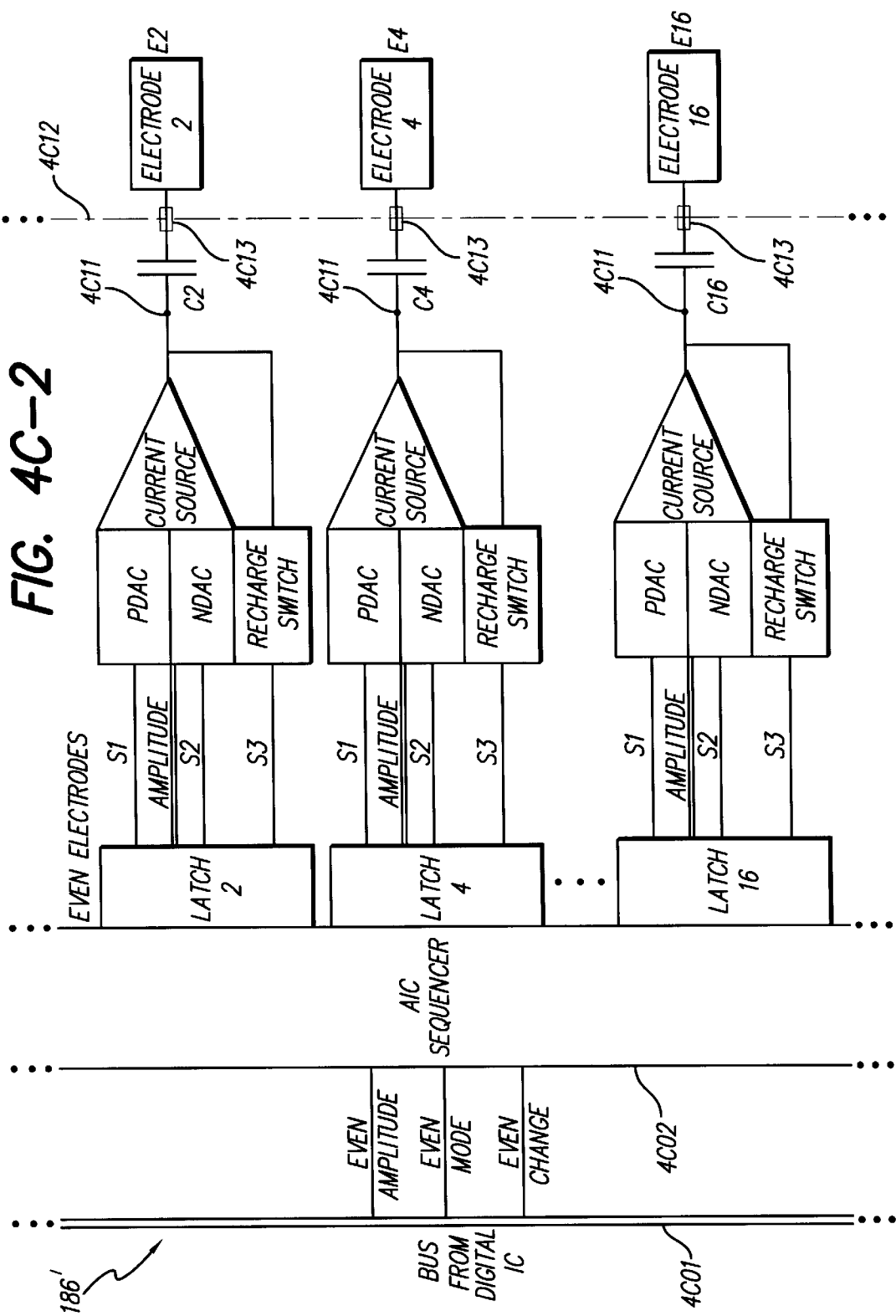

IMPLANTABLE DEVICE PROGRAMMER

The present application claims the benefit of U.S. Provisional patent application Serial No. 60/169,129, filed Dec. 6, 1999, which application is incorporated herein by reference.

BACKGROUND OF THE INVENTION

The present invention relates to implantable medical devices, and more particularly to a programmer used to program such medical devices. In accordance with one embodiment, the invention relates to a programmer adapted for use with an implantable spinal cord stimulator (SCS), or similar implantable neural stimulator, and relates to the manner in which the paresthesia resulting from applied electrical stimuli is adjusted or programmed so as to match an area of perceived pain or other need.

Many types of implantable nerve stimulators exist which perform the function of providing selected electrical stimulation through selected groupings of implanted electrodes. An example of such a nerve stimulator is a spinal cord stimulator. One type of spinal cord stimulation system is disclosed in applicants' copending patent application, "Rechargeable Spinal Cord Stimulator System", Ser. No. 09/626,010, filed Jul. 26, 2000, which application is incorporated herein by reference. One way of controlling the operating parameters used to control such a spinal cord stimulator is disclosed in applicants' copending application, "Parameter Context Switching For An Implanted Device," Ser. No. 09/668,925, filed Sep. 25, 2000, which application is also incorporated herein by reference. A preferred way of sensing and setting the stimulation parameters associated with such a spinal cord stimulator is taught in applicant Mann's copending application, "Magnitude Programming for Implantable Electrical Stimulator", Ser. No. 60/172,167, now U.S. Pat. No. 6,381,496 B1, which patent is likewise incorporated herein by reference.

Spinal cord stimulation systems offer a large number of variables to be programmed. For example, in addition to the variables of stimulation frequency and stimulation current amplitude, the number of electrode contacts that provide the stimulation must be programmed. Moreover, because such selected electrode contacts are typically selected from a relatively large number of contacts, with the number of possible electrode combinations being a large number, there is a need to determine which electrode combination from such large number of possible combinations, provides the optimum stimulation performance for the patient. That is, after initial implantation, it is typically necessary to program many electrode combinations and to test the patient response to each combination. This can be a very time consuming task, both to perform the selected programming of all the electrode combinations, and then to conduct the testing for each selected combination. Optimal device settings, i.e., an optimal electrode combination, is highly dependent upon the location and distribution of stimulating current provided through the selected electrode combination relative to various nerve paths of the body, which in turn varies significantly from patient to patient. Thus, one selected electrode combination that proves effective for one patient, may not prove effective for another patient. Hence, many different electrode combinations must be programmed and tested in a relatively short period of time in order to discover which electrode combination is most effective for a given patient.

Heretofore, the process of optimizing the stimulator device settings has typically involved having the programming clinician simply select an electrode combination and stimulation settings, wait for a patient response, and then intuitively or arbitrarily make changes to the programming in response to patient feedback, wherein the goal is to affect the pain site by paresthesia. (Herein, "paresthesia" is a term used to describe the tingling sensation felt by a patient as a result of application of an electrical stimulus.) Much research has been published showing spinal cord mapping in relation to anatomical areas and neurophysiologic responses to help understand how best electrode arrays should be set up, or programmed, for effective stimulation. Spinal cord mapping has also been associated to dermatome segments of the body.

In U.S. Pat. No. 5,370,672, one way is taught by which an implanted device may be programmed. In accordance with the teachings of the '672 patent, a patient is provided with a touch sensitive screen on which a representation of the human body is presented. The touch sensitive screen is connected to a suitable computer, and the computer is linked with the implanted device, i.e., stimulus commands may be sent from the computer to the implanted device. The patient then draws a circle around the area of pain he or she is experiencing on the touch sensitive screen using a stylet or other suitable tool. Acting on that information, the computer sends commands to the stimulator to activate an electrode combination in the vicinity of the identified pain area. The patient then draws another circle on the touch sensitive screen indicating where he or she feels the paresthesia resulting from the applied stimulus. The computer then calculates, using predetermined rules, a new electrode combination in an attempt to bring the paresthesia drawing closer to the pain drawing, and then sends a new command to the stimulator to cause it to apply an electrical stimulus to the new electrode combination. The patient responds by drawing another circle on the touch sensitive screen indicating where he or she feels the paresthesia resulting from the stimulus applied to the newly selected electrode combination. This process continues, using the paresthesia location information provided by the patient after stimulating each new electrode combination, in an attempt to bring or move the paresthesia-patient-identified area on the touch sensitive screen over the pain area, initially identified on the touch sensitive screen by the patient. Disadvantageously, this approach requires additional hardware in addition to the programming computer, including a touch sensitive screen and a stylet.

What is needed is a more streamlined approach for programming an implanted device that does not require the use of additional hardware other than the programming computer.

BRIEF SUMMARY OF THE INVENTION

The present invention addresses the above and other needs by allowing a patient to program an implant device, e.g., an implanted spinal cord stimulator (SCS), so that the area of sensed paresthesia resulting from applied electrical stimuli matches the perceived area of pain. Such programming is accomplished through the use of a programming computer, e.g., a laptop or personal handheld computer, linked with the implant device. The computer is programmed to utilize information known in the art regarding anatomical relationships between the spine and the body. The body is divided into dermatomes and/or subdivisions of dermatomes, and a representation of the body, including its dermatomes and/or subdivisions of dermatomes are displayed on the screen (or other display device) associated with the computer. The patient then moves a cursor over the regions of the body displayed on the computer screen. As the patient thus moves the cursor over regions of the body, dermatones or body subdivisions are exposed, allowing the patient to select the region of pain or paresthesia by a click of a mouse or the press of a button.

For example, in one implementation, the patient may select a region of pain by a right mouse click, and a region of paresthesia by a left mouse click. Advantageously, the patient may select as many dermatomes or body segments/regions/subdivisions as necessary to communicate the area of pain or paresthesia to the computer. The computer then uses this information to quickly zero in on an electrode combination and appropriate stimulus parameters so as to create a match (or as close of a match as is possible) between the pain region and the paresthesia region.

One aspect of the invention is directed to a method of programming an implant device. The implant device typically comprises an implantable pulse generator having an implantable electrode array connected thereto. The implantable pulse generator has electrical circuitry therein that generates electrical stimulation pulses in accordance with programming data. The electrical stimulation pulses are delivered to body tissue of a patient through a selected combination of a multiplicity of electrodes on the electrode array. The programming method taught by the invention generally includes the following steps:

(a) creating a data base that maps various electrode combinations to paresthesia regions of the body based on known and collected data;

(b) storing the data base in a programming computer;

(c) displaying a human figure on a display screen of the programming computer, and dividing the human figure into a multiplicity of regions;

(d) selecting one region on the displayed human figure where the patient feels pain;

(e) selecting a combination of electrodes and stimulation parameters adapted to produce paresthesia in the region of pain;

(f) generating stimulation pulses and delivering the stimulation pulses to the selected combination of electrodes through the implantable pulse generator;

(g) identifying a region of paresthesia on the displayed human figure where the stimulation pulses generated in step (f) produce paresthesia;

(h) determining the degree of mismatch between the region of paresthesia identified in step (f) and the region of pain selected in step (d);

(i) if the degree of mismatch exceeds a prescribed level, selecting a new combination of electrodes and stimulation parameters based on the identified region of paresthesia and the degree of mismatch, and repeating steps (f), (g) and (h); and (j) if the degree of mismatch is less than the prescribed level, programming the implantable pulse generator with the programming data that produces the least mismatch.

Another aspect of the invention is directed to a system for programming an implantable pulse generator. The implantable pulse generator has an implantable electrode array connected thereto. Further, the implantable pulse generator has electrical circuitry therein that generates electrical stimulation pulses in accordance with programming data. These electrical stimulation pulses may be delivered to body tissue of a patient through a selected combination of a multiplicity of electrodes on the electrode array. The system for programming includes the following components:

(a) a programming computer linked to the implantable pulse generator. The programming computer has a display screen, and includes means for generating and displaying a cursor on the screen that may be manually moved around on the screen by a user.

(b) means in the computer for displaying a human figure on the display screen, where the human figure is divided into a multiplicity of regions.

(c) means coupled to the computer for selecting a region on the displayed human figure where the patient feels pain. If necessary, more than one region may be selected (e.g., if the patient feels pain in more than one region).

(d) means in the computer for automatically selecting a combination of electrodes and stimulation parameters adapted to produce paresthesia in the selected region(s) of pain. This selection will initially be made based on information previously programmed into the computer, e.g., a data base, that defines known anatomical relationships between the spine and the body.

(e) means for generating stimulation pulses and delivering the stimulation pulses to the selected combination of electrodes through the implantable pulse generator.

(f) means for identifying a region(s) of paresthesia on the displayed human figure where the stimulation pulses generated in step (e) produce paresthesia.

(g) means in the computer for determining the degree of mismatch between the identified region(s) of paresthesia and the selected region(s) of pain.

(h) means in the computer for selecting a new combination of electrodes and stimulation parameters based on the identified region(s) of paresthesia and the degree of mismatch if the degree of mismatch exceeds a prescribed level. Then, generating stimulation pulses using the new combination of electrodes and stimulation parameters and determining a new degree of mismatch between the pain and paresthesia regions. This process is then repeated as necessary, thereby minimizing in an iterative fashion the degree of mismatch.

(i) means for programming the implantable pulse generator with the programming data that produces the least mismatch.

Yet another aspect of the invention is directed to a programming apparatus for programming an implantable pulse generator. The implantable pulse generator comprises electrical circuitry that generates electrical stimulation pulses controlled by programming data stored in the computer. An electrode array having a multiplicity of electrodes is coupled to the electrical circuitry. Such programming apparatus includes the following elements:

(1) a programming computer linked to the implantable pulse generator, where the programming computer has a display screen, and means for generating and displaying a cursor or equivalent marker on the display screen that may be manually moved around on the display screen by a user;

(2) first program data stored in the programming computer that causes a human figure to be displayed on the display screen, where the human figure is divided into a multiplicity of regions;

(3) means coupled to the cursor for selecting at least one region on the displayed human figure as a location where the patient feels pain;

(4) second program data stored in the programming computer that causes a combination of electrodes and stimulation parameters to be selected that are adapted to produce paresthesia in the same general location where the patient feels pain;

(5) third program data stored in the programming computer that determines the degree of mismatch between the location where the patient feels pain and the location where the patient feels paresthesia as a result of stimulation pulses produced by the second program data;

(6) fourth program data stored in the programming computer that causes a new combination of electrodes and stimulating parameters to be selected that are adapted to minimize the degree of mismatch between the location where the patient feels pain and the location where the patient feels paresthesia as a result of recently applied stimulation pulses; and (7) fifth program data stored in the programming computer that causes the combination of electrodes and stimulation parameters that minimize the degree of mismatch to be included in the programming data that thereafter controls the operation of the implantable pulse generator.

It is thus a feature of the present invention to provide a programming device for use with an implantable stimulator, such as an implantable spinal cord stimulator, that allows the patient to easily identify a region of pain and then a region of paresthesia, so that the programming device may then automatically change the selected stimulation parameters, including the selected combinations of electrodes, to cause the region of paresthesia to overlap or merge with the region of pain, thereby alleviating the pain.

BRIEF DESCRIPTION OF THE DRAWINGS

The above and other aspects, features and advantages of the present invention will be more apparent from the following more particular description thereof, presented in conjunction with the following drawings wherein:

FIGS. 4C-1, 4C-2 and 4C-3, referred to collectively as FIG. 4C, show a block diagram, spread over three drawing sheets, of the analog integrated circuit (AIC) used, intra alia, to provide the output of the stimulus generators within the IPG hybrid architecture shown in FIG. 4B;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

At the outset, it is emphasized that the present invention relates to an implantable device programmer, i.e., a method or system for programming, or programming apparatus for use with, an implant device so that the implant device carries out a desired function. The invention will be described with reference to the implanted pulse generator (IPG) used as part of a spinal cord stimulation (SCS) system. An exemplary SCS system is described more fully in previously referenced U.S. patent applications, Ser. Nos. 09/626,010, 09/668,925 and 60/172,167, now U.S. Pat. No. 6,381,496 B1. It is to be understood, however, that the present invention is not limited for use just within an SCS system of the type described in the referenced patent applications. Rather, the invention has broad applicability, and may be used with numerous different types of implant devices and systems used to alleviate pain or produce other desired results, and wherein feedback from the patient may be obtained regarding areas or regions where paresthesia or other sensations are felt as a result of applied electrical stimuli. Such systems may include all types of neural stimulators and sensors, deep brain stimulators, cochlear stimulators, drug delivery systems, muscle tissue stimulators, and the like.

Figure 1:
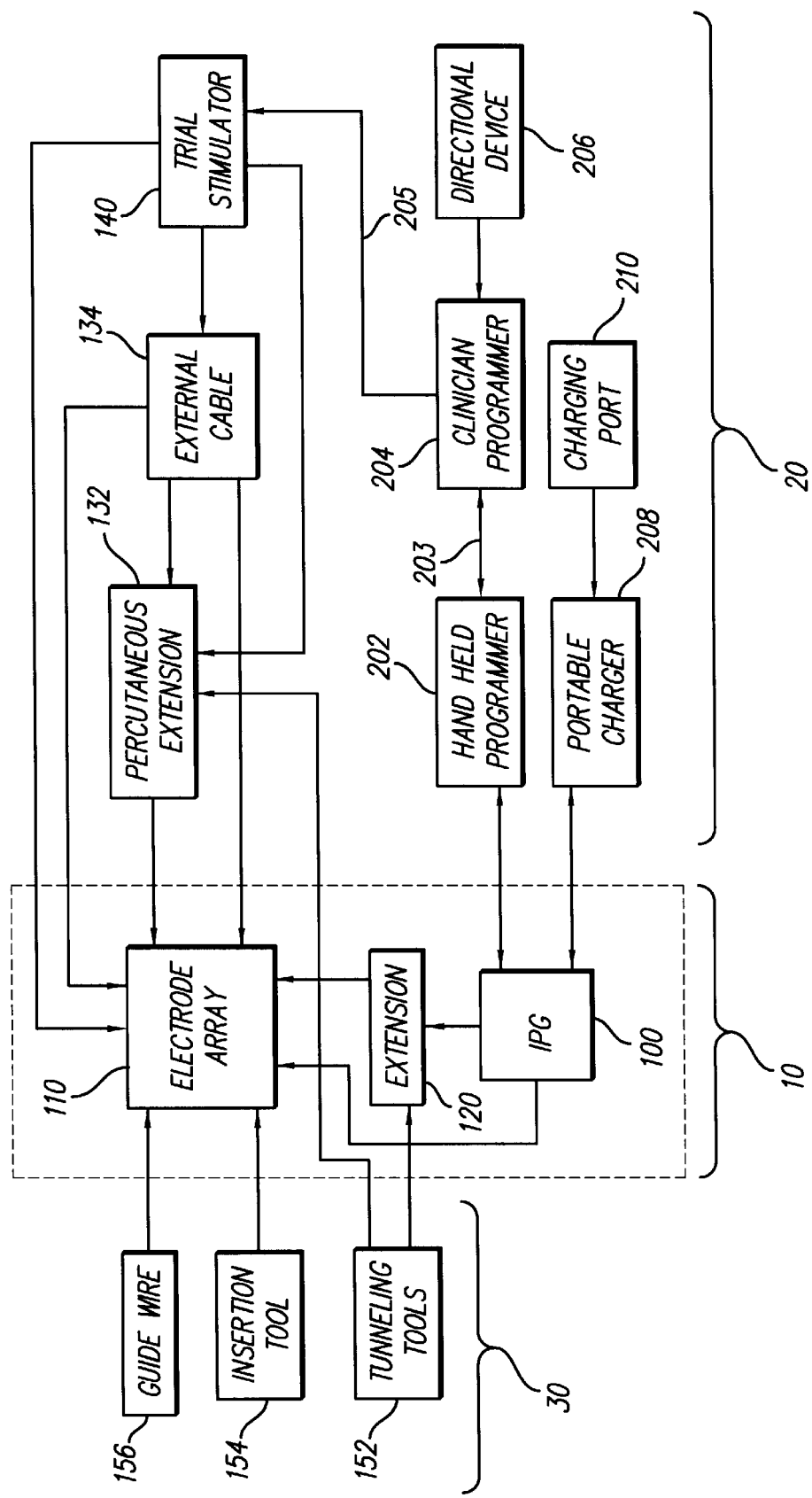
FIG. 1 is a block diagram that illustrates the various implantable, external, and surgical components of a representative implantable stimulation system.

Turning first to FIG. 1, there is shown a block diagram that illustrates the various components of an exemplary SCS system, including an implantable pulse generator (IPG) and hand-held programmer (HHP) used with such system. These components may be subdivided into three broad categories: (1) implantable components 10, (2) external components 20, and (3) surgical components 30. As seen in FIG. 1, the implantable components 10 include an implantable pulse generator (IPG) 100, an electrode array 110, and (as needed) an extension 120. The extension 120 is used to electrically connect the electrode array 110 to the IPG 100. Different embodiments of a suitable IPG 100 are described more fully below in connection with FIG. 4A and FIG. 4B. The IPG 100 described below comprises a rechargeable, multichannel, telemetry-controlled, pulse generator. A suitable connector allows the electrode array 110 or extension 120 to be detachably secured, i.e., electrically connected, to the IPG 100.

The IPG 100 contains stimulating electrical circuitry ("stimulating electronics"), a power source, e.g., a rechargeable battery, and a telemetry system. Typically, the IPG 100 is placed in a surgically-made pocket either in the abdomen, or just at the top of the buttocks. It may, of course, also be implanted in other locations of the patient's body. Once implanted, the IPG 100 is connected to the lead system, comprising the lead extension 120, if needed, and the electrode array 110. The lead extension 120, for example, may be tunneled up to the spinal column. Once implanted, the lead system 110 and lead extension 120 are intended to be permanent. In contrast, the IPG 100 may be replaced when its power source fails or is no longer rechargeable.

Figure 2:
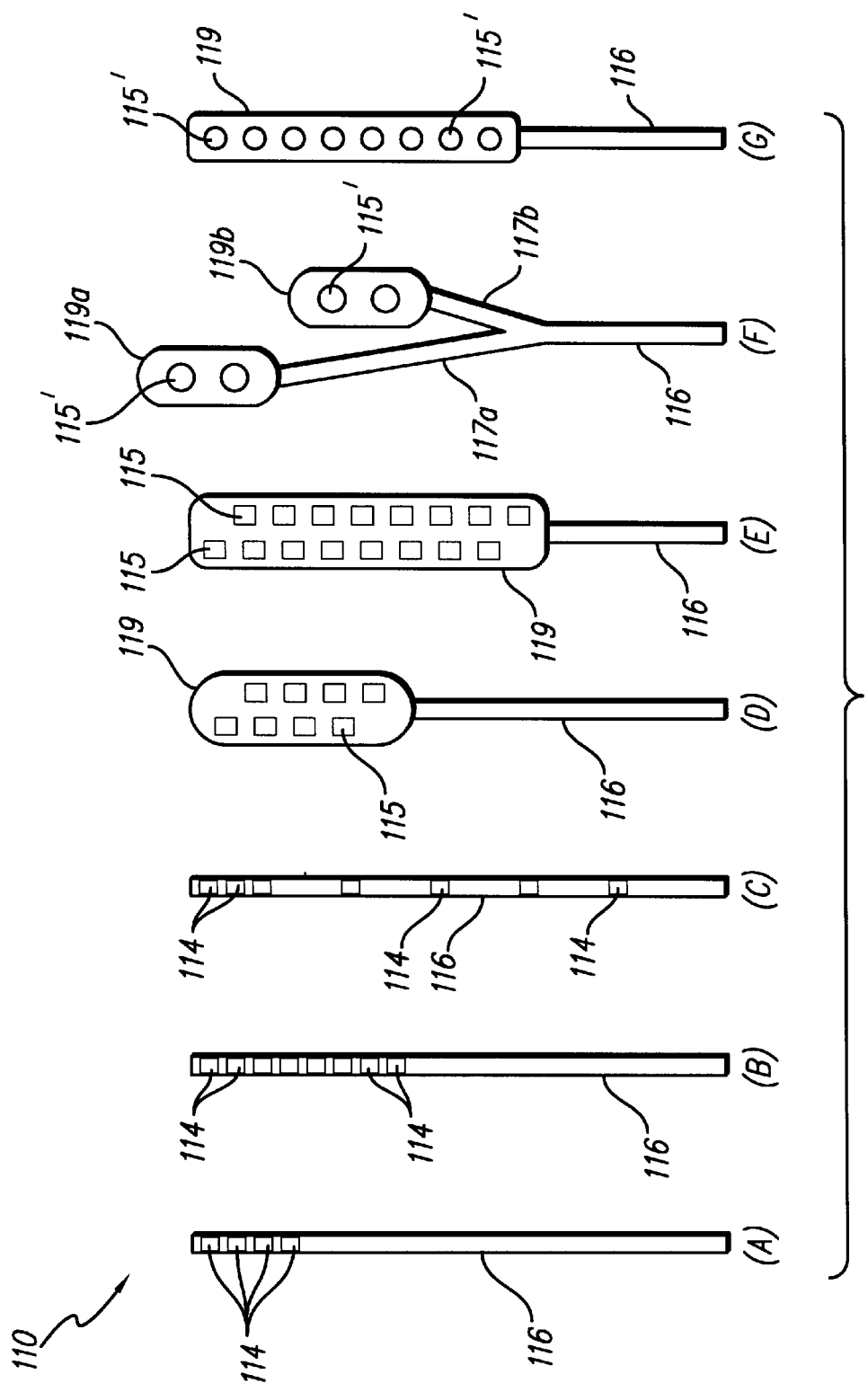
FIG. 2 illustrates examples of various types of electrode arrays that may be used with the system of FIG. 1.

Advantageously, the IPG 100 can provide electrical stimulation through a multiplicity of electrodes, e.g., sixteen electrodes, included within the electrode array 110. Different types of electrode arrays 110 that may be used with the invention are depicted in FIG. 2. A common type of electrode array 110, for example, is the "in-line" lead, as shown at (A), (B), and (C) in FIG. 2. An in-line lead includes individual electrode contacts 114 spread longitudinally along a small diameter flexible cable or carrier 116. The flexible cable or carrier 116 has respective small wires embedded (or otherwise carried therein) for electrically contacting each of the individual electrode contacts. The advantage of an in-line lead relates to its ease of implantation, i.e., it can be inserted into the spinal canal through a small locally-anesthetized incision while the patient is kept awake. When the patient is awake, he or she can provide valuable feedback as to the effectiveness of stimulation applied to a given electrode contact or contacts 114 for a given positioning of the array 110. One of the disadvantages of the in-line lead is that it is prone to migrating in the epidural space, either over time or as a result of a sudden flexion movement. Such migration can disadvantageously change the location and nature of the paresthesia and the required stimulation level. Either or both of the these conditions may require reprogramming of the IPG 100 and/or surgical correction (repositioning) of the electrode array 110. Note, as used herein, the term "paresthesia" refers to that area or volume of the patient's tissue that is affected by the electrical stimuli applied through the electrode array. The patient may typically describe or characterize the paresthesia as an area where a tingling sensation is felt.

To overcome the migration problems associated with an in-line electrode, a different type of electrode array 110 may be used, known as a paddle lead. Various types of paddle leads are illustrated at (D), (E), (F) and (G) of FIG. 2. In general, each type of paddle lead is shaped with a wide platform 119 on which a variety of electrode contact configurations or arrays are situated. For example, the paddle lead shown at (D) in FIG. 2 has two columns of four rectangular-shaped electrode contacts 115 carried on a wide platform 119, with the electrode contacts in one column being offset from the electrode contacts in the other column. (Here, the term "offset" refers to the vertical position of the electrode contacts, as the leads are oriented in FIG. 2.) The flexible cable or carrier 116 carries wires from each electrode contact to a proximal end of the paddle lead (not shown), where such wires may be connected to the IPG 100 (or to a lead extension 119, which in turn connects to the IPG 100). The paddle lead shown at (E) in FIG. 2 similarly has two columns of eight electrode contacts 115 in each row, with the electrode contacts in one column being offset from the electrode contacts in the other column, and with each electrode contact being connected to one or more wires carried in the flexible cable or carrier 116.

Still referring to FIG. 2, other types of paddle leads are illustrated. As seen at (F) in FIG. 2, one type of paddle lead has its carrier or cable 116 branch into two separate branches 117a and 117b, with a wide platform 119a and 119b being located at a distal end of each branch. Within each wide platform 119a and 119b an array of at least two circular-shaped electrode contacts 115' is situated. As seen in (G) in FIG. 2, another type of paddle lead has a wide platform 119 at its distal end on which a single column of circular-shaped electrode contacts 115' is situated.

Still other types of leads may be used with the IPG 100 (FIG. 1) in addition to the representative leads shown in FIG. 2. For example, the deployable electrode array disclosed in U.S. patent application Ser. No. 09/239,927, filed Jan. 28, 1999, now U.S. Pat. No. 6,205,361, represents still another type of lead and electrode array that may be used with the invention. The '361 patent is incorporated herein by reference.

Whichever type of lead and electrode array is used, an important feature of the SCS system shown in FIG. 1 is the ability to support more than one lead with two or more channels. Here, a "channel" is defined as a specified electrode, or group of electrodes, that receive a specified pattern or sequence of stimulus pulses. Thus, where more than one "channel" is available, each channel may be programmed to provide its own specified pattern or sequence of stimulus pulses to its defined electrode or group of electrodes. In operation, all of the stimulus patterns applied through all of the channels of such multi-channel system thus combine to provide an overall stimulation pattern that is applied to the tissue exposed to the individual electrodes of the electrode array(s).

There are many instances when it is advantageous to have multiple channels. For example, left and right sides, or upper and lower extremities, may require different stimulus parameter settings. Low back pain typically requires a different stimulation site and stimulation parameters than any of the extremities. Moreover, many patients exhibit conditions better suited to horizontal stimulation paths, while other patients may have conditions better suited to vertical stimulation paths. Therefore, having multiple channels that may be connected to multiple electrodes, positioned within one or more electrode arrays, so as to cover more tissue/nerve area, greatly facilitates providing the type of stimulation pattern and stimulation parameters needed to treat a particular patient.

One type of preferred electrode configuration uses a multiple lead system, e.g., two or four leads, with the leads placed side by side, or at different vertical locations. The individual electrodes on each vertical lead of such multiple lead system effectively create a desired electrode array that covers a large, or relatively large, tissue area. The respective electrodes of each vertical lead may be aligned horizontally, offset horizontally, or randomly or systematically arranged in some other pattern.

The electrode array 110 and its associated lead system typically interface with the implantable pulse generator (IPG) 100 via a lead extension system 120. As needed, e.g., for testing and/or fitting purposes, the electrode array 110 may also interface with an external trial stimulator 140 through one or more percutaneous lead extensions 132, connected to the trial stimulator 140 through an external cable 134. In this manner, the individual electrodes included within the electrode array 110 may receive an electrical stimulus from either the trial stimulator 140 or the IPG 100.

As suggested in the block diagram of FIG. 1, the lead extension(s) 120, as well as the percutaneous extension(s) 132, are inserted through the patient's tissue through the use of appropriate surgical components 30, and in particular through the use of tunneling tools 152, as are known in the art, or as are especially developed for purposes of spinal cord stimulation systems. In a similar manner, the electrode array 110 is implanted in its desired position, e.g., adjacent the spinal column of the patient, through the use of an insertion needle 154 and a guide wire 156.

Figure 3:
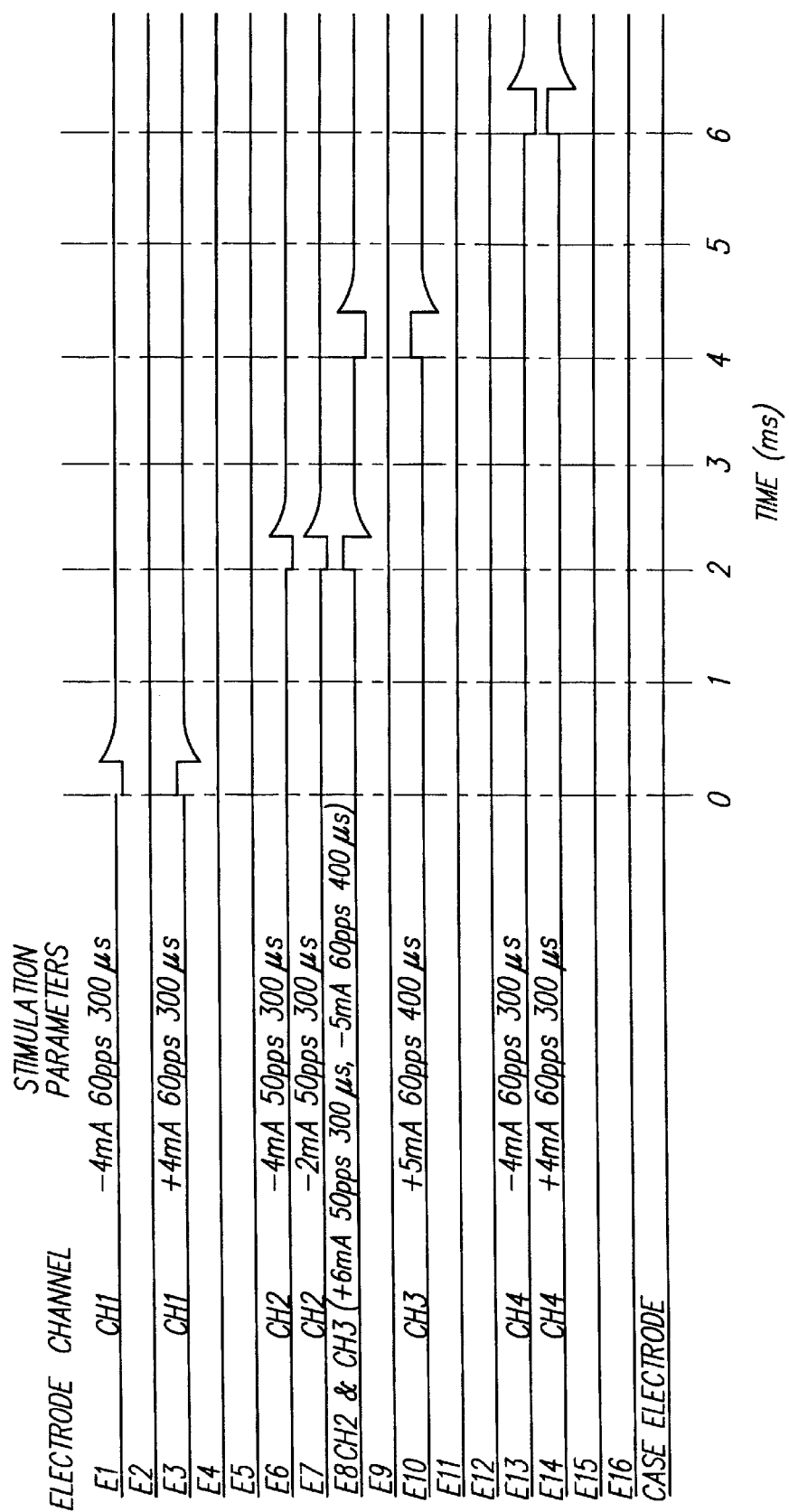
FIG. 3 is a timing waveform diagram that depicts representative current waveforms that may be applied to various ones of the electrode contacts of the electrode arrays through one or more stimulus channels.

The operation of multiple channels used to provide a stimulus pattern through multiple electrodes is illustrated in FIG. 3. FIG. 3 assumes the use of an electrode array 110 having sixteen electrodes connected to the implantable pulse generator (IPG) 100. In addition to these sixteen electrodes, which are numbered E1 through E16, a case electrode (or return electrode) is also available. In FIG. 3, the horizontal axis is time, divided into increments of 1 millisecond (ms), while the vertical axis represents the amplitude of a current pulse, if any, applied to one of the sixteen electrodes. Thus, for example, at time t=0 ms, FIG. 3 illustrates that a current pulse of 4 milliamps (mA) appears on channel 1 at electrode E1 and E3. FIG. 3 further shows that this current pulse is negative (−4 mA) on electrode E1 and positive (+4 mA) on electrode E3. Additionally, FIG. 3 shows that the stimulation parameters associated with this current pulse are set at a rate of 60 pulses per second (pps), and that the width of the pulse is about 300 microseconds ($\mu$s).

Still with reference to FIG. 3, it is seen that at time t=2 ms, channel 2 of the IPG 100 is set to generate and apply a 6 mA pulse, having a repetition rate of 50 pps and a width of 300 $\mu$s, between electrode E8 (+6 mA) and electrodes E6 and E7 (−4 mA and −2 mA, respectively). That is, channel 2 of the IPG supplies a current pulse through electrode E8 (+6 mA) that is shared on its return path through electrode E6 (−4 mA) and electrode E7 (−2 mA).

As further seen in FIG. 3, at time t=4 ms, channel 3 of the IPG 100 is set to generate and supply a 5 mA pulse to electrode E10 (+5 mA) which is returned through electrode E8 (−5 mA). This pulse is provided at a rate of 60 pps, and a width of 400 $\mu$s. Similarly, it is seen that at time t=6 ms, channel 4 of the IPG is set to generate and supply a 4 mA pulse to electrode E14 (+4 mA) which is returned through electrode E13 (−4 mA). This channel 4 pulse has a rate of 60 pps and a width of 300 $\mu$s.

The particular electrodes that are used with each of the four channels of the IPG 100 illustrated in FIG. 3 are only exemplary of many different combinations of electrode pairing and electrode sharing that could be used. That is, any channel of the IPG may be programmably connected to any grouping of the electrodes, including the reference (or case) electrode. While it is typical that only two electrodes be paired together for use by a given channel of the IPG, as is the case with channels 1, 3 and 4 in the example of FIG. 3, it is to be noted that any number of electrodes may be grouped and used by a given channel. When more than two electrodes are used with a given channel, the sum of the current sourced from the positive electrodes should be equal to the sum of the current sunk (returned) through the negative electrodes, as is the case with channel 2 in the example of FIG. 3 (+6 mA sourced from electrode E8, and a total of −6 mA sunk to electrodes E6 [−4 mA] and E7 [−2 mA]).

In a preferred embodiment, the IPG has sixteen electrode contacts, each of which is independently programmable relative to stimulus polarity and amplitude for each of up to four different programmable channel assignments (groups or phase generators). In operation, each channel identifies which electrodes among the sixteen electrodes, E1, E2, E3 . . . E16 and the IPG case electrode (reference electrode), are to output stimulation pulses in order to create an electric current field. All electrodes assigned to a given channel deliver their stimulation pulses simultaneously with the same pulse width and at the same pulse rate. For each channel, the IPG case electrode is programmable either as a Positive (passive anode) or OFF. Thus, monopolar stimulation is provided when the only electrode contact programmed to Positive is the IPG case electrode, and at least one other electrode is programmed to Negative. For each of the other electrodes, E1, E2, E3 . . . E16, on each channel, the polarity is programmable to: (1) Negative (cathode), with associated negative current amplitude; (2) Positive (anode), with an associated positive current limit amplitude; or (3) Off.

Because of power limitations within the IPG, the average stimulus current delivered by the IPG during all active phase periods may be limited. An "active" phase period is a phase period of the stimulus current during which the stimulus current is being provided by one or more of available turned ON current sources. In contrast, a "passive" phase period (also sometimes referred to as a "recharge" phase period) is a phase period of the stimulus current during which the current sources are turned OFF, and the stimulus current results from a recharge or redistribution of the charge flowing from the coupling capacitance present in the stimulus circuit.

Net DC charge transfer is prevented during stimulation through the use of coupling capacitors C1, C2, C3, . . . C16 (see FIG. 4A or 4C) between the electrodes E1, E2, E3, . . . E16 and the IPG output.

To prevent patient discomfort due to rapidly increasing or decreasing amplitudes of stimulus current, a slow start/end feature may be employed wherein changes in amplitude are limitable to occur slowly and smoothly over a transition period.

To prevent more than one channel from producing a stimulus current at the same time, i.e., to prevent current pulses from different channels that overlap, an overlap arbitration circuit may be optionally employed (that is, an arbitration feature may be programmed ON or OFF for each channel) that determines which channel has priority. The arbitration circuit, in a preferred embodiment, functions in accordance with the following principles. Once a non-overlapping channel begins a pulse, the start of pulses from any other non-overlapping channel is delayed until the ongoing pulse phase one is completed and a Hold-Off period has been completed. The Hold-Off period is timed from the end of the first phase of the pulse. If the start of two or more non-overlapping channels are delayed by an ongoing pulse and Hold-Off period, the pending channels are started in the order they would have occurred without arbitration.

Figure 4A:
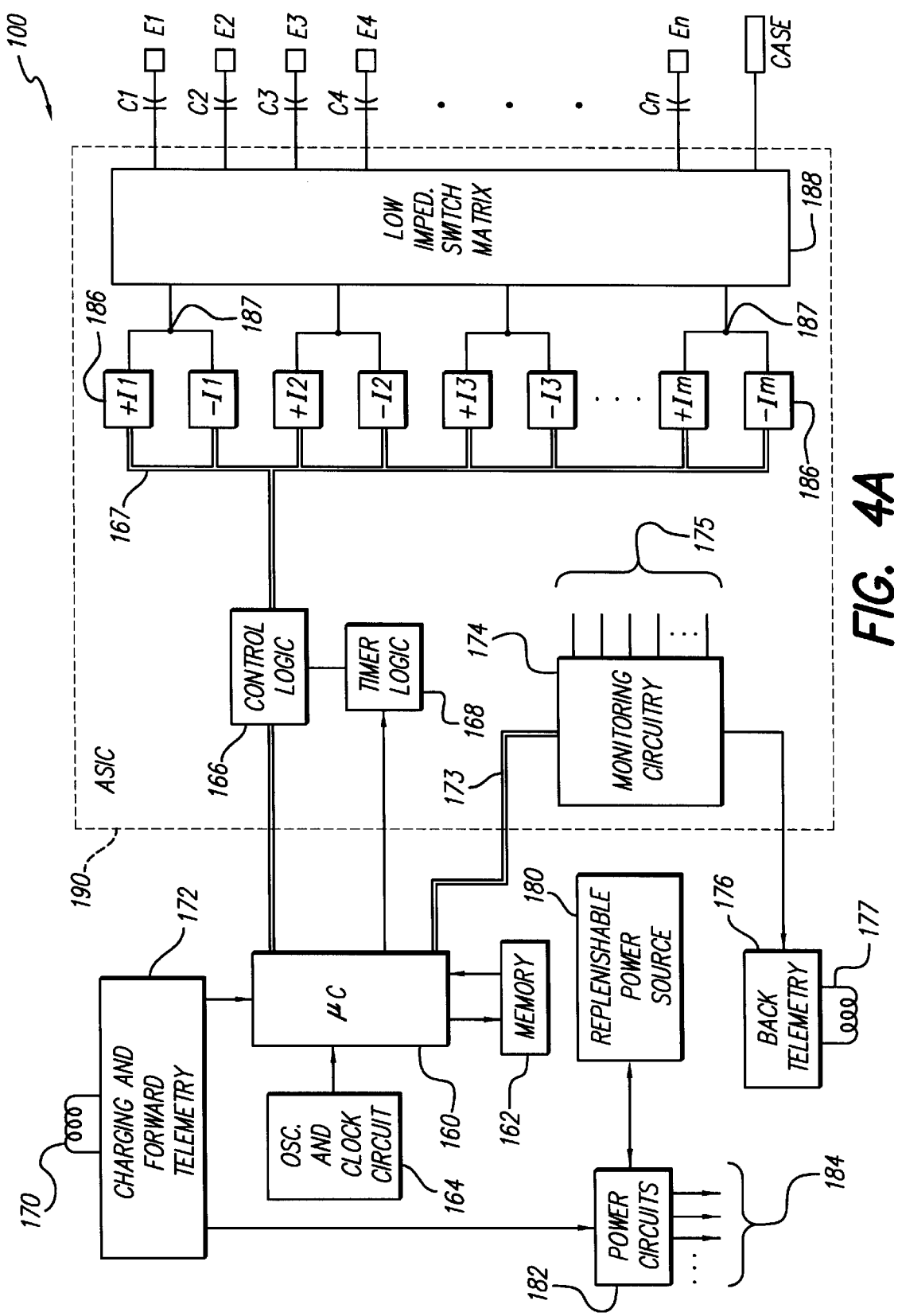
FIG. 4A is a block diagram that illustrates the main components of a representative implantable pulse generator that may be used with the invention.

Next, turning to FIG. 4A, a block diagram is shown that illustrates the main components of one embodiment of an implantable pulse generator, or IPG 100, that may be used with an SCS system (or other neural stimulation system) in accordance with the invention. As seen in FIG. 4A, the IPG includes a microcontroller ($\mu$C) 160 connected to memory circuitry 162. The $\mu$C 160 typically comprises a microprocessor and associated logic circuitry, which in combination with control logic circuits 166, timer logic 168, and an oscillator and clock circuit 164, generate the necessary control and status signals which allow the $\mu$C to control the operation of the IPG in accordance with a selected operating program and stimulation parameters. The operating program and stimulation parameters are typically programmably stored within the memory 162 by transmitting an appropriate modulated carrier signal through a receiving coil 170 and charging and forward telemetry circuitry 172 from an external programing unit, e.g., a handheld programmer (HHP)

202 and/or a clinician programmer (CP) 204, assisted as required through the use of a directional device 206 (see FIG. 1). (The handheld programmer is thus considered to be in "telecommunicative" contact with the IPG; and the clinician programmer is likewise considered to be in telecommunicative contact with the handheld programmer, and through the handheld programmer, with the IPG.) The charging and forward telemetry circuitry 172 demodulates the carrier signal it receives through the coil 170 to recover the programming data, e.g., the operating program and/or the stimulation parameters, which programming data is then stored within the memory 162, or within other memory elements (not shown) distributed throughout the IPG 100.

Still with reference to FIG. 4A, the microcontroller 160 is further coupled to monitoring circuits 174 via bus 173. The monitoring circuits 174 monitor the status of various nodes or other points 175 throughout the IPG 100, e.g., power supply voltages, current values, temperature, the impedance of electrodes attached to the various electrodes E1 . . . En, and the like. Informational data sensed through the monitoring circuit 174 may be sent to a remote location external the IPG (e.g., a non-implanted location) through back telemetry circuitry 176, including a transmission coil 177.

The operating power for the IPG 100 is derived from a replenishable power source 180, e.g., a rechargeable battery and/or a supercapacitor. Such power source 180 provides an unregulated voltage to power circuits 182. The power circuits 182, in turn, generate the various voltages 184, some of which are regulated and some of which are not, as needed by the various circuits located within the IPG. The power circuits 182 further selectively direct energy contained within the carrier signal, obtained through the charging and forward telemetry circuit 172, to the replenishable power source 180 during a charging mode of operation. In this way, the power source 180 may be recharged when needed.

In a preferred embodiment, the power source 180 of the IPG 100 comprises a rechargeable battery, and more particularly a rechargeable Lithium Ion battery. Recharging occurs inductively from an external charging station. While recharging is shown in FIG. 4A as occurring through the forward telemetry coil 170, it is noted that recharging may also occur through the back-telemetry coil 177 or through a separate charging coil. Because the SCS IPG 100 could accept or receive a charge from an unauthorized source, internal battery protection circuitry is employed, for safety reasons, to protect the battery (e.g., to prevent the battery from being overcharged and/or to accept a charge only from an authorized charging device). Also, safeguarding features are incorporated that assure that the power source, e.g., battery, is always operated in a safe mode upon approaching a charge depletion.

Additionally, the IPG 100 is able to monitor and telemeter the status of its replenishable power source 180 (e.g., rechargeable battery) each time a communication link is established with the external patient programmer 202, or at other select times. Such monitoring not only identifies how much charge is left, but also charge capacity. Typically, each time a programming event occurs, i.e., each time the patient or medical personnel change a stimulus parameter, or initiate a charging operation, a telecommunicative link is established with the implant device, and hence battery monitoring may occur.

Still with reference to FIG. 4A, it is seen that a plurality m of independent current source pairs, 186+I1,186−I1,186+I2,186−I2,186+I3,186−I3, . . . 186+Im, 186−Imare coupled to the control logic 166 via control bus 167. One current source of each pair of current sources functions as a positive (+) current source, while the other current source of each pair functions as a negative (−) current source. The output of the positive current source and the negative current source of each pair of current sources 186 is connected to a common node 187. This common node 187, in turn, is connected through a low impedance switching matrix 188 to any of n electrode nodes E1, E2, E3, . . . En, through respective coupling capacitors C1, C2, C3, . . . Cn. (Note: a second embodiment of the IPG, see FIGS. 4B and 4C, discussed below, does not use a low impedance switching matrix 188. Rather, in the second embodiment, there is an independent bi-directional current source for each of the sixteen electrodes.) Through appropriate control of the switching matrix 188, when used (FIG. 4A); or through operation of the independent bi-directional current sources, when used (FIGS. 4B and 4C); any of the m current source nodes 187 may be connected to any of the electrode nodes E1, E2, E3, . . . En. Thus, for example, it is possible to program the current source 186+I1 to produce a pulse of +4 mA (at a specified rate and for a specified duration), and to synchronously program the current source 186−I2 to similarly produce a pulse of −4 mA (at the same rate and pulse width), and then connect the 186+I1 node 187 to electrode node E3 and the 186−I2 node to electrode node E1 at relative time t=0 ms (and at a recurring rate thereafter) in order to realize the operation of channel 1 depicted in the timing diagram of FIG. 3. In a similar manner, the operation of channels 2, 3 and 4 shown in FIG. 3 may likewise be realized.

As described, it is thus seen that any of the n electrodes may be assigned to up to k possible groups (where k is an integer corresponding to the number of channels, and in a preferred embodiment is equal to 4). Moreover, any of the n electrodes can operate, or be included in, any of the k channels. The channel identifies which electrodes are selected to synchronously source or sink current in order to create an electric field. Amplitudes and polarities of electrodes on a channel may vary, e.g., as controlled by the patient hand held programmer (HHP) 202. External programming software in the clinician programmer 204 is typically used to assign a pulse rate and pulse width for the electrodes of a given channel.

Thus, it is seen that each of the n programmable electrode contacts can be programmed to have a positive (sourcing current), negative (sinking current), or off (no current) polarity in any of the k channels.

Advantageously, each of the n electrode contacts can operate in a bipolar mode or multipolar mode, e.g., where two or more electrode contacts are grouped to source/sink current at the same time. Alternatively, each of the n electrode contacts can operate in a monopolar mode where, e.g., the electrode contacts associated with a channel are configured as cathodes (negative), and the case electrode, on the IPG case, is configured as an anode (positive).

Further, the amplitude of the current pulse being sourced or sunk from a given electrode contact may be programmed to one of several discrete levels. In order to prevent "jolts", current amplitude changes may be gradually changed, e.g., in a ramping fashion, from one value to another within the range of values available between the settings. Such ramping feature is also used when initially powering on the IPG, thereby preventing full magnitude stimulus pulses from being delivered to the patient during a ramping-up time period, and a ramping-down period is used when powering off the IPG. The ramping-up and ramping-down time periods may vary, depending upon the channel and programmed amplitude, between about 1 and 10 seconds. Also, in one embodiment, the pulse width of the current pulses is adjustable in convenient increments. Similarly, in one embodiment, the pulse rate is adjustable within acceptable limits.

The stimulation pulses generated by the IPG 100 are typically charged balanced. This means that the amount of positive charge associated with a given stimulus pulse must be offset with an equal and opposite negative charge. Charge balance may be achieved through a coupling capacitor, which provides a passive capacitor discharge that achieves the desired charge balanced condition. Such passive capacitor discharge is evident in the waveforms depicted in FIG. 3 as the slowly decaying waveform following the short trailing edge of each pulse. Alternatively, active biphasic or multiphasic pulses with positive and negative phases that are balanced may be used to achieve the needed charge balanced condition.

In some embodiments of the invention, a real-time clock is also incorporated within the timing circuits of the IPG 100. Such real-time clock advantageously allows a run schedule to be programmed. That is, the patient can schedule auto-run times for IPG operation at certain times of the day. When an auto-run time begins, all channels are enabled and provide a previously-programmed pattern of stimulus currents, i.e., current pulses having a programmed width, rate, and amplitude are generated and delivered through each channel. The auto-run time continues for a set time period, e.g., several hours, or for only a few minutes. When a programming change is made by the patient or other medical personnel, the auto-run time, when enabled at the programmed time of day, invokes the most recent programming changes made to each channel.

An important feature included within the IPG 100 is its ability to measure electrode impedance, and to transfer the impedance thus measured back to a remote programmer, or other processor, through the back telemetry circuits 176. Also, the microcontroller 160, in combination with the other logic circuits, may also be programmed to use the electrode impedance measurements to adjust compliance voltages and to thereby better maintain low battery consumption. For a spinal cord implantation, the electrode impedance will typically range between about 400 ohms and 1000 ohms.

The type of current sources depicted in FIG. 4A may be realized by those of skill in the art using any suitable circuitry. For example, the teachings of International Patent Application Serial Number PCT/US99/14190, filed Jun. 23, 1999, entitled "Programmable Current Output Stimulus Stage for Implantable Device", published as International Publication No. WO-00/00251, on Jan. 6, 2000, could be used. The WO-00/00251 publication is incorporated herein by reference.

As shown in FIG. 4A, much of circuitry included within the embodiment of the IPG 100 illustrated in FIG. 4A may be realized on a single application specific integrated circuit (ASIC) 190. This allows the overall size of the IPG 100 to be quite small, and readily housed within a suitable hermetically-sealed case.

Figure 4B:
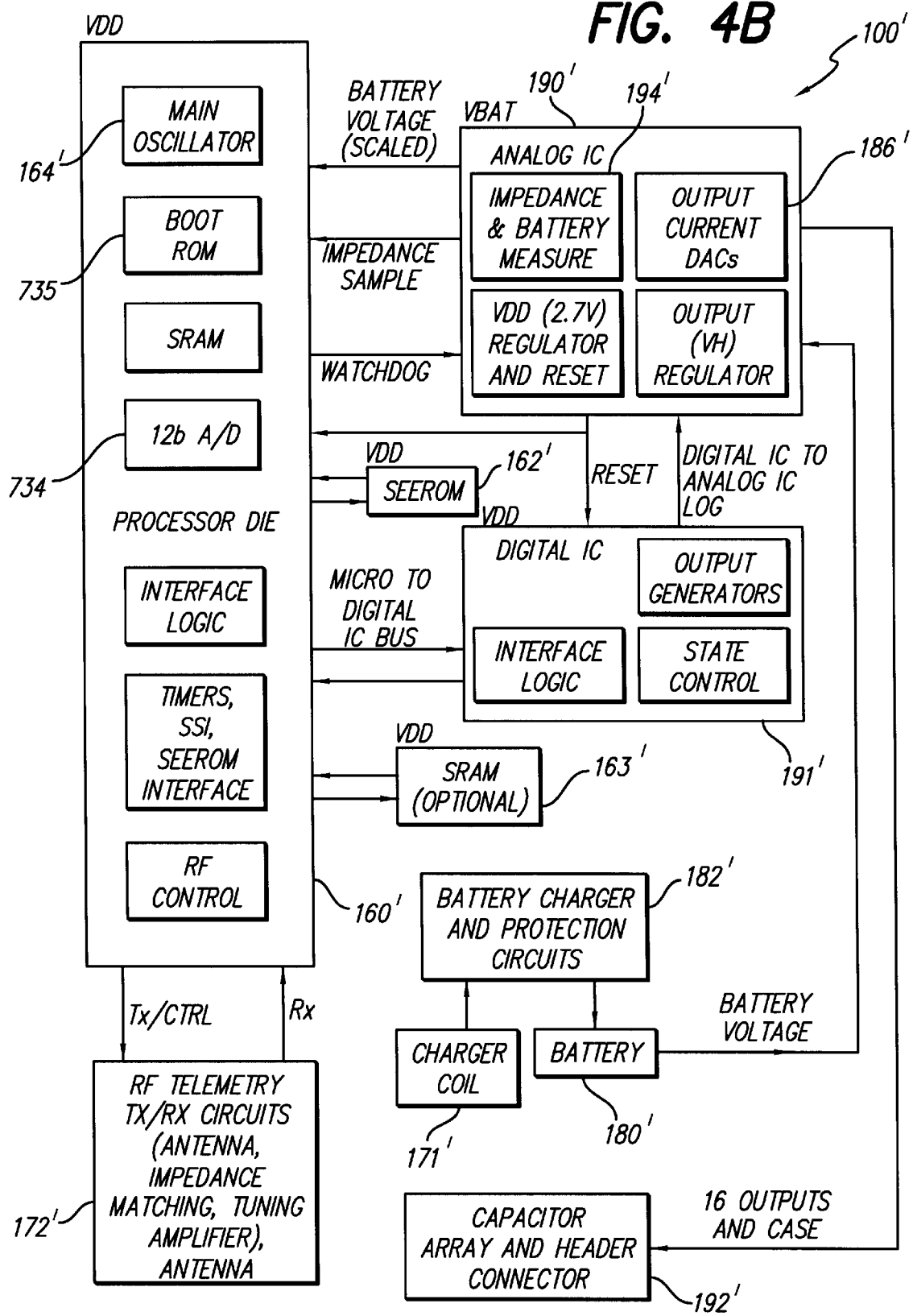
FIG. 4B shows an IPG hybrid block diagram that illustrates the architecture of an IPG made in accordance with a second IPG embodiment of the invention.

Turning next to FIG. 4B, a hybrid block diagram of an alternative embodiment of an IPG 100' that may be used with the invention is illustrated. The IPG 100' includes both analog and digital dies, or integrated circuits (IC's), housed in a single hermetically-sealed rounded case. Many of the circuits contained within the IPG 100' are identical or similar to the circuits contained within the IPG 100, shown in FIG. 4A. The IPG 100' includes a processor die, or chip, 160', an RF telemetry circuit 172' (typically realized with discrete components), a charger coil 171', a lithium ion battery 180', battery charger and protection circuits 182', memory circuits 162' (SEEROM) and 163' (SRAM), a digital IC 191', an analog IC 190', and a capacitor array and header connector 192'.

The capacitor array and header connector 192' includes 16 output decoupling capacitors, as well as respective feed-through connectors for connecting one side of each decoupling capacitor through the hermetically-sealed case to a connector to which the electrode array 110, or lead extension 120, may be detachably connected.

The processor 160' is realized with an application specific integrated circuit (ASIC) that comprises the main device for full bi-directional communication and programming. The processor 160' utilizes an 8086 core (the 8086 is a commercially-available microprocessor), 16 kilobytes of SRAM memory, two synchronous serial interface circuits, a serial EEPROM interface, and a ROM boot loader. The processor die 160' further includes an efficient clock oscillator circuit 164' and a mixer and modulator/demodulator circuit implementing the QFAST RF telemetry method supporting bi-directional telemetry at, 8 Kbits/second. QFAST stands for "Quadrature Fast Acquisition Spread Spectrum Technique", and represents a known and viable approach for modulating and demodulating data (see U.S. Pat. No. 5,559,828). An analog-to-digital converter (A/D) circuit 734 is also resident on the processor 160' to allow monitoring of various system level analog signals, impedances, regulator status and battery voltage. The processor 160' further includes the necessary communication links to other individual ASIC's utilized within the IPG 100'.

The analog IC (AIC) 190' comprises an ASIC that functions as the main integrated circuit that performs several tasks necessary for the functionality of the IPG 100', including power regulation, stimulus output, and impedance measurement and monitoring. Electronic circuitry 194' performs the impedance measurement and monitoring function. The main area of the analog 190' is devoted to the current stimulus generators 186'. These generators 186' may be realized using the circuitry described in the previously-referenced PCT application, International Publication No. WO-00/00251, or similar circuitry. Regulators for the IPG 100' supply the processor and the digital sequencer with a suitable voltage, e.g., 2.7 V ±10%. Digital interface circuits residing on the AIC 190' are similarly supplied with a suitable operating voltage, e.g., 2.7 V ±10%. A regulator that is programmable from, e.g., 5V to 18V, supplies the operating voltage for the output current DACs 186'.

Figures 1, 4C:
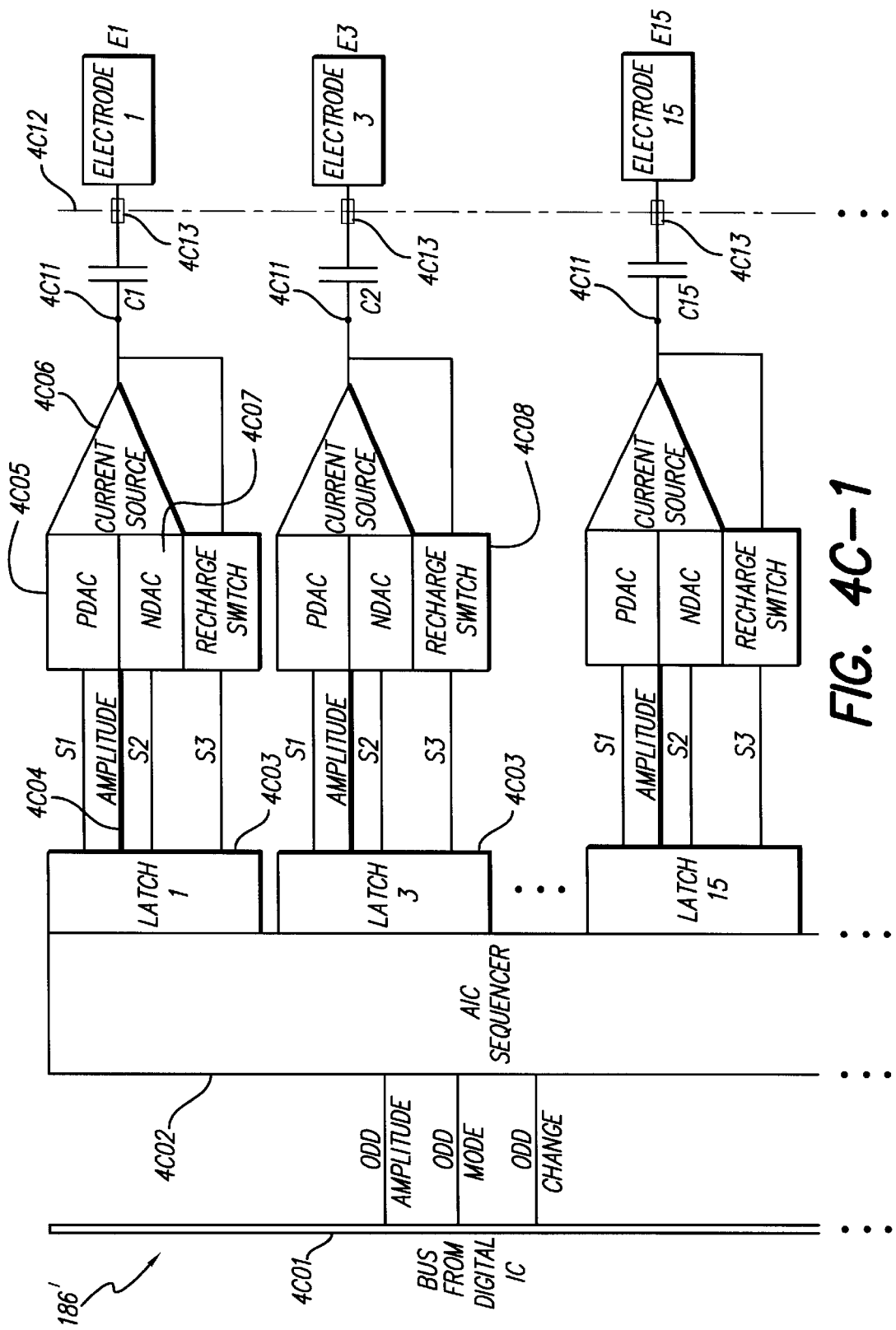
Figures 3, 4C:
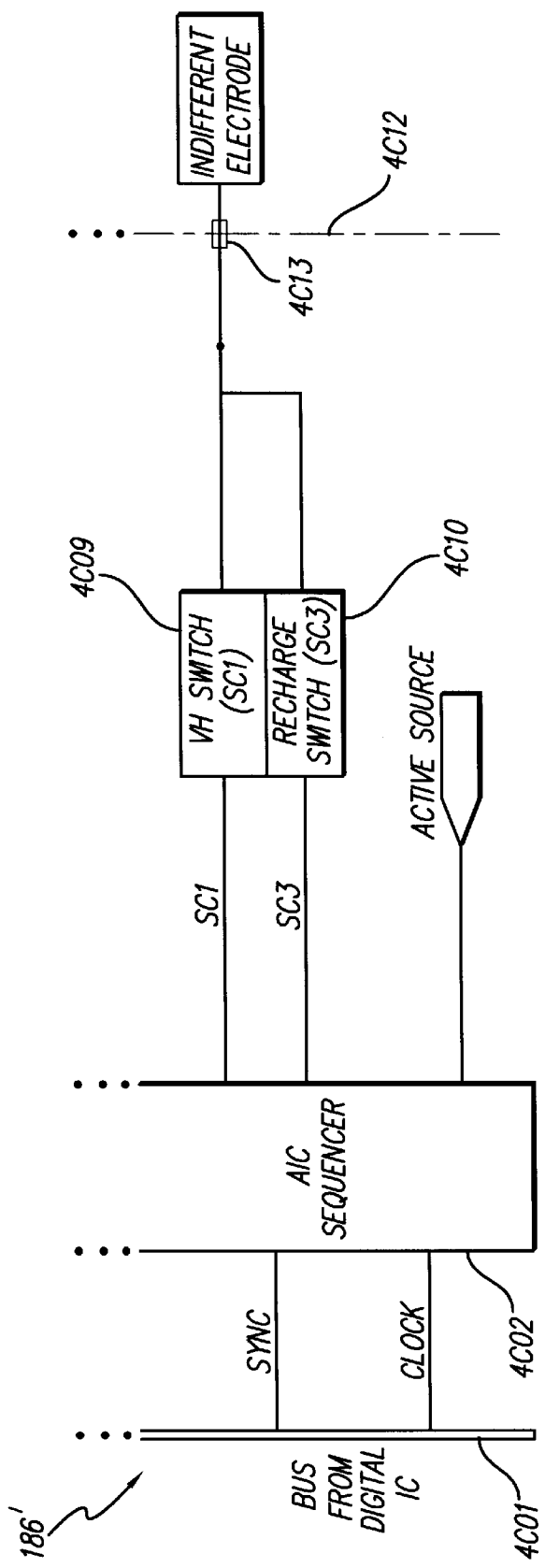

A block diagram of the output stimulus generators 186' included within the AIC 190' is shown in FIG. 4C. As seen in FIG. 4C, which figure is spread over three separate sheets, and labeled FIGS. 4C-1, 4C-2 and 4C-3, a data bus 4C01 from the digital IC 191' couples data received from the digital IC to AIC sequencer circuits 4C02. Such data includes odd and even amplitude data, odd and even mode data, and odd and even change data, where "odd" and "even" refer to the electrode number (with electrodes E1, E3, E5, etc. being "odd" electrodes; and electrodes E2, E4, E6, etc., comprising "even" electrodes). A multiplicity of latch circuits 4C03 are connected to the AIC sequencer 4C02, one latch circuit for each electrode. Hence, where there are sixteen electrodes, E1, E2, . . . E16, there are sixteen identical latch circuits 4C03. Each latch circuit includes an amplitude bus 4C04 on which the amplitude data is placed, an S1 line for designating a positive amplitude, an S2 line for designating a negative amplitude, and an S3 line for designating a recharge state. A PDAC circuit 4C05 is enabled by a signal on the S1 line when a current having the amplitude specified on the amplitude bus 4C04 is to be sourced from a current source 4C06 through a coupling capacitor Cn, where n is an integer from 1 to 16. Similarly, an NDAC circuit 4C07 is enabled by a signal on the S2 line when a current having the amplitude specified on the amplitude bus 4C04 is to be sunk into the current source 4C06 through the coupling capacitor Cn. A recharge switch 4C08 is enabled by the signal on the S3 line when it is desired to remove the charge from the coupling capacitor Cn. Another switch 4C09 allows an indifferent electrode 4C11, e.g., the case of the IPG, to be turned on upon receipt of an SC1 signal. Similarly, a recharge switch 4C10 allows the indifferent electrode 4C11 to be selectively connected to ground, or another voltage source, upon receipt of an SC2 signal.

Thus, from FIG. 4C, it is seen that the analog IC 186' includes a multiplicity of output current sources 4C06, e.g., sixteen bi-directional output current sources, each configured to operate as a DAC current source. Each DAC output current source 4C06 may source or sink current, i.e., each DAC output current source is bi-directional. Each DAC output current source is connected to an electrode node 4C11. Each electrode node 4C11, in turn, is connected to a coupling capacitor Cn. The coupling capacitors Cn and electrode nodes, as well as the remaining circuitry on the analog IC 186', are all housed within the hermetically sealed case of the IPG 100. The dashed-dotted line 4C12 represents the boundary between the sealed portion of the IPG case and the unsealed portion. A feedthrough pin 4C13, which is included as part of the header connector 192' (FIG. 4B), allows electrical connection to be made between each of the coupling capacitors Cn and the respective electrodes E1, E2, E3 . . . , or E16, to which the DAC output current source is associated.

Returning again to FIG. 4B, a digital IC (DigIC) 191' is also provided as part of the IPG 100' that functions as the primary interface between the processor 160' and the AIC output circuits 186'. The main function of the DigIC 191' is to provide stimulus information to the output current generator register banks. The Dig IC 191' thus controls and changes the stimulus levels and sequences when prompted by the processor 160'.

The RF circuitry 172' includes antennas and preamplifiers that receive signals from the HHP 202 and provide an interface at adequate levels for the demodulation/modulation of the communication frames used in the processor 160'. Any suitable carrier frequency may be used for such communications. In a preferred embodiment, the frequency of the RF carrier signal used for such communications is 262.144 KHz, or approximately 262 MHz.

The Battery Charger and Protection Circuits 182' provide battery charging and protection functions for the Lithium Ion battery 180'. A charger coil 171' inductively (i.e., electromagnetically) receives rf energy from the external charging station. The battery charger circuits perform three main functions: (1) during normal operation, they continually monitor the battery voltage and provide charge status information to the patient at the onset of a communication link, (2) they ensure that the battery is not over-discharged, and (3) they monitor the battery voltage during a charging cycle to ensure that the battery does not experience overcharging.

As described above, it is thus seen that the implant portion 10 of the SCS system of the present invention (see FIG. 1) includes an implantable pulse generator (IPG) 100 or 100' as described in FIGS. 4A–4C. Such IPG further includes stimulating electronics (comprising programmable current sources and associated control logic), a power source, and a telemetry system. Advantageously, the power source may be recharged over and over again, as needed, and may thus provide a long life, as well as a high current output capacity.

An important feature of the present invention is its ability to map current fields through selective control of the current sources which are attached to each electrode node. In one preferred embodiment, the invention achieves its desired function of being able to independently map a desired current to each electrode node through the use of a processor 160', one or more ASIC's 190' or 191', sixteen independent bi-directional output current DACs (FIG. 4C, elements 4C05–4C07), and timers and control registers, configured to operate in a state machine architecture. The ASIC has a standard bus interface to the microcontroller allowing simple, direct and efficient access to all of its control and stimulation parameter registers. Triggering and timing control circuitry allow the simultaneous activation of any of the channels. In one embodiment (FIG. 4A), a low impedance switching matrix advantageously allows the mapping of each current generator's two outputs to be assigned to any of the pulse generator electrode nodes (or leadwires, which are attached to the electrode nodes) or to the case. In another embodiment (FIGS. 4B and 4C), there is no need for a low impedance switching matrix. Rather, independent bi-directional current sources for each of the sixteen electrodes (independently operable output current DACs) allow the output currents to be mapped to any of the output electrode nodes or to the case. In this manner, one or more current generators may be attached to any one or more electrode nodes (leadwires) and thus electrodes, and conversely, any electrode node (leadwire) may be attached to one or more current generator outputs, grounded, or left open. The significance of the biphasic, or (in some instances) multiphasic, nature of the stimulation pulses is that currents may be actively driven in either the anodic or cathodic direction to the output electrode nodes of the current generators. This feature, along with the matrix switching of output leads, or independently operable output current DACs, depending upon the embodiment used, allows the creation of "virtual" electrodes and stimulation current field control, not possible with other known designs. This feature thus provides an important advance in the ability to direct the stimulation pulses to pools of target neurons in the spinal cord.

Once the IPG 100 has been implanted, and the implant system 10 is in place, the system is programmed to provide a desired stimulation pattern at desired times of the day. The stimulation parameters that can be programmed include the number of channels (defined by the selection of electrodes with synchronized stimulation), the stimulation rate and the stimulation pulse width. The current output from each electrode is defined by polarity and amplitude. Additionally, as indicated above, a run schedule may be downloaded and stored in the memory of the IPG 100, which when used enables (or turns on) the IPG at pre-programmed times of the day.

The back telemetry features of the IPG 100 advantageously allow the status of the IPG to be checked. For example, when the external hand-held programmer 202 (and/or the clinician programmer 204) initiates a programming session with the implant system 10 (FIG. 1), the capacity of the battery is telemetered so that the external programmer can calculate the estimated time to recharge. Additionally, electrode impedance measurements are telemetered at the beginning of each programming session, or as requested. Any changes made to the current stimulus parameters are confirmed through back telemetry, thereby assuring that such changes have been correctly received and implemented within the implant system. Moreover, upon interrogation by the external programmer, all programmable settings stored within the implant system 10 may be uploaded to one or more external programmers.

Next, the clinician programming system will briefly be described. This system includes, as seen in FIG. 1, a clinician programmer 204 coupled to a directional device 206. The clinician programmer 204 typically interfaces with a patient hand-held programmer (HHP) 202 in communicating with the implanted pulse generator (IPG) 100. However, other types of communication links between the clinician programmer 204 (also referred to herein as a programming computer) and the IPG 100 may be utilized.

The programming system maintains a patient data base, and is able to program all features of the implant device in a simple and intuitive manner. Preprogrammed into the data base, along with information about the patient, is known information regarding anatomical relationships between the spine and the body. Additionally, the system allows threshold measurements to be made, operational electrodes to be identified, and is able to interface directly with the patient.

A key feature of the SCS programming system is the use of a joystick accessory, or equivalent directional device 206 (FIG. 1), which allows the patient to interface with a laptop computer (e.g., programmed to function as the clinician programmer 204), or other processor (e.g., a hand-held computer, such as a PalmPilot® computer, or equivalent) so as to allow the patient, or other medical personnel assisting the patient, to configure electrodes and adjust various stimulation parameters and to identify regions of the body where pain is present and where a paresthesia is felt. One suitable directional programming device is described in more detail in U.S. Pat. No. 6,052,624, entitled "Directional Programming for Implantable Electrode Arrays", which patent is incorporated herein by reference. As described in the '624 patent, such directional programming may advantageously be performed either in the operating room (OR) environment and in the doctor's office. The clinician or nurse simply operates the joystick feature, or equivalent directional programming feature, during surgery in conjunction with the trial stimulator 140 so as to configure and select the electrodes that provide desired stimulation. The patient then uses the joystick feature to finalize the device programming during a post implant adjustment session. Thus, whether communicating with the trial stimulator 140 or with the IPG 100, the directional programming device 206 is able to be effectively used to configure which electrodes provide stimuli to the patient.

The directional programming device may take many forms. For purposes of the present invention, any device that allows a computer-generated cursor (or other indicator) to move about on the display screen of the computer as controlled by the user will suffice. Representative directional programming devices include keys on a keyboard (e.g., arrow keys), a mouse, a track ball, a touch-sensitive screen over which the users finger may be moved, voice commands in combination with voice recognition software, light sensors on which a light beam, e.g., a laser wand, may be directed, and the like.

In operation, as seen in FIG. 1, the clinician programming system communicates to the patient HHP 202 over a telecommunicative or other communication link 203, which then telemeters the data to the IPG 100. Likewise, the clinician's programmer is able to communicate to the trial stimulator 140 over the telecommunicative link 205. The communication links 203 and 205 are reliable links capable of operating in the busy OR environment. Data speeds to and from the IPG 100, through the patient programmer 202 intermediary link, are fast enough to not noticeably delay programming. A communication link status between devices is always depicted on a screen, or other display device, associated with the programmer 204.

As soon as the clinician programmer is initially connected to the implant system, hardware recognition occurs. That is, the system identifies the stimulator, the patient programmer, and electrode availability (through electrode impedance measurements).

For safety, the patient programmer 202 is coded to work only with a specific implant system. Should the patient lose his or her programmer 202, then the physician, using the clinician programmer, is able to code a new programmer for use with the patient's implant system. The clinician's programmer, in contrast, is able to communicate to any implant through any programmer 202 by using an overriding universal code. This allows the patient code to be extracted from the IPG 100 and used to re-code a new programmer 202.

When an IPG 100 is in contact with a clinician programmer 204, the device settings and hardware information (model, serial number, number of electrode by impedance, and the like) are first uploaded to the clinician programmer 204. All devices in the link with the IPG, e.g., the hand held device 202, and/or the trial stimulator 140, and clinician programmer 204, and the clinician programmer 204, are synchronized so that each device receives accurate and current data. Programming changes made to the stimulator (s) are confirmed through back telemetry or other means before the SCS add-on software reflects the change. Advantageously, the physician is able to program the stimulator through either the patient programmer 202 or the clinician programmer 204 while linked together through the link 203, with all programming changes being mirrored in both devices.

Additional details associated with the Clinician's programming system are more fully described in the previously referenced U.S. patent application Ser. No. 09/626,010.

Figure 5:
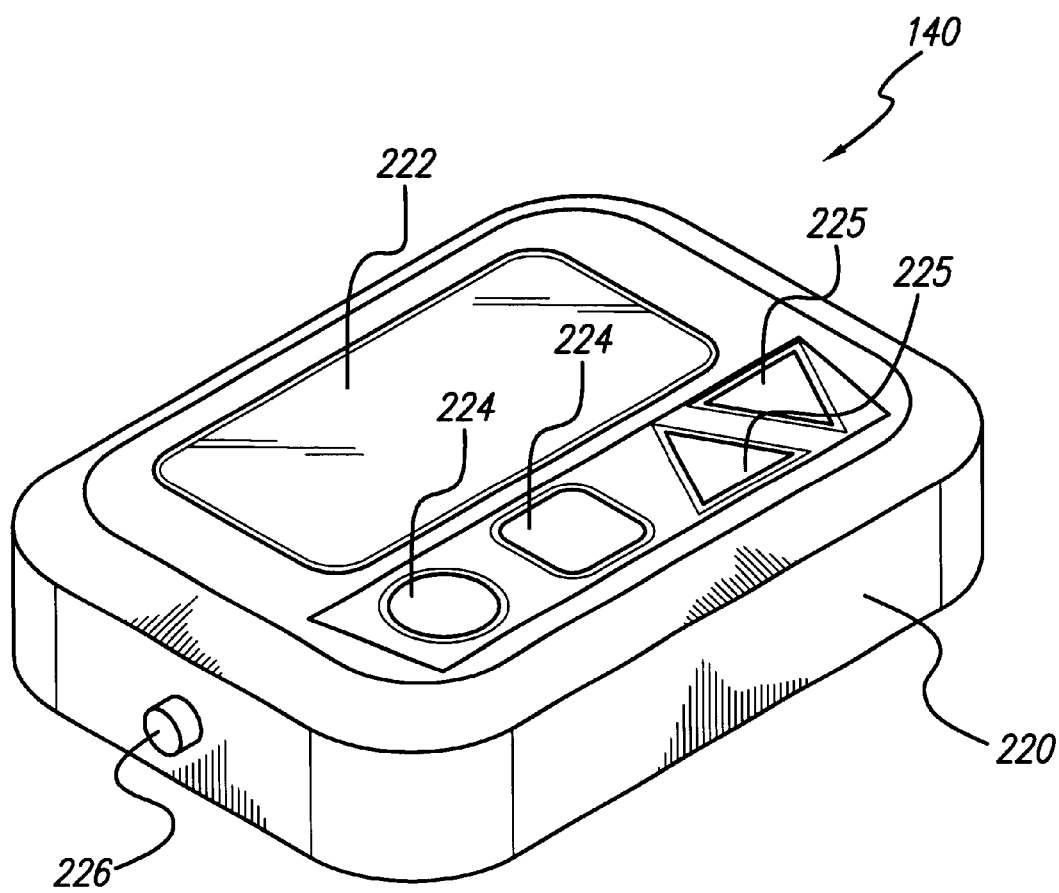
FIG. 5 illustrates a type of hand-held programmer that may be used to program the IPG.

Turning next to FIG. 5, one type of hand-held programmer (HHP) 202 that may be used as a component of the exemplary SCS system is illustrated. As seen in FIG. 5, the HHP 202 is housed within a hand-held case 220. Displayed on the case 220 are a set of intuitive control buttons 224, 225 that control the operation of the device. Advantageously, the HHP 202 is compact in size, and can be easily held in one hand. To make it even easier to carry, especially by the patient, a belt clip is placed on its back side, thereby allowing it to be worn on a patient belt, much like a pager or cell-phone. The device case includes an accessible battery compartment wherein replaceable (and/or rechargeable) batteries may be carried having sufficient capacity to provide operating power to its internal circuitry for at least one week.

A more detailed description of the patient handheld programmer (HHP) 202 may be found in the previously referenced patent applications Ser. Nos. 09/626,010 or 09/668,925.

The SCS further provides a programming window that facilitates programming the stimulator, or IPG. The programming window may, in one embodiment, include tiered sub-windows, which may be titled, e.g., "measurements", "programming", and "advanced".

The measurement window, which may also be referred to as a "threshold" window, is used to set maximum and minimum thresholds, and to map pain and paresthesia with implanted electrodes to anatomical sites in accordance with the present invention. Mapping of maximum and minimum thresholds is preferably done in a way that normalizes the measured threshold values for each channel to fall within a range of "1" (minimum threshold) to "10" (maximum threshold), as described more fully in the previously-referenced copending patent application Ser. No. 60/172, 167, filed Dec. 17, 1999, now U.S. Pat. No. 6,381,496 B1.

Figure 6:
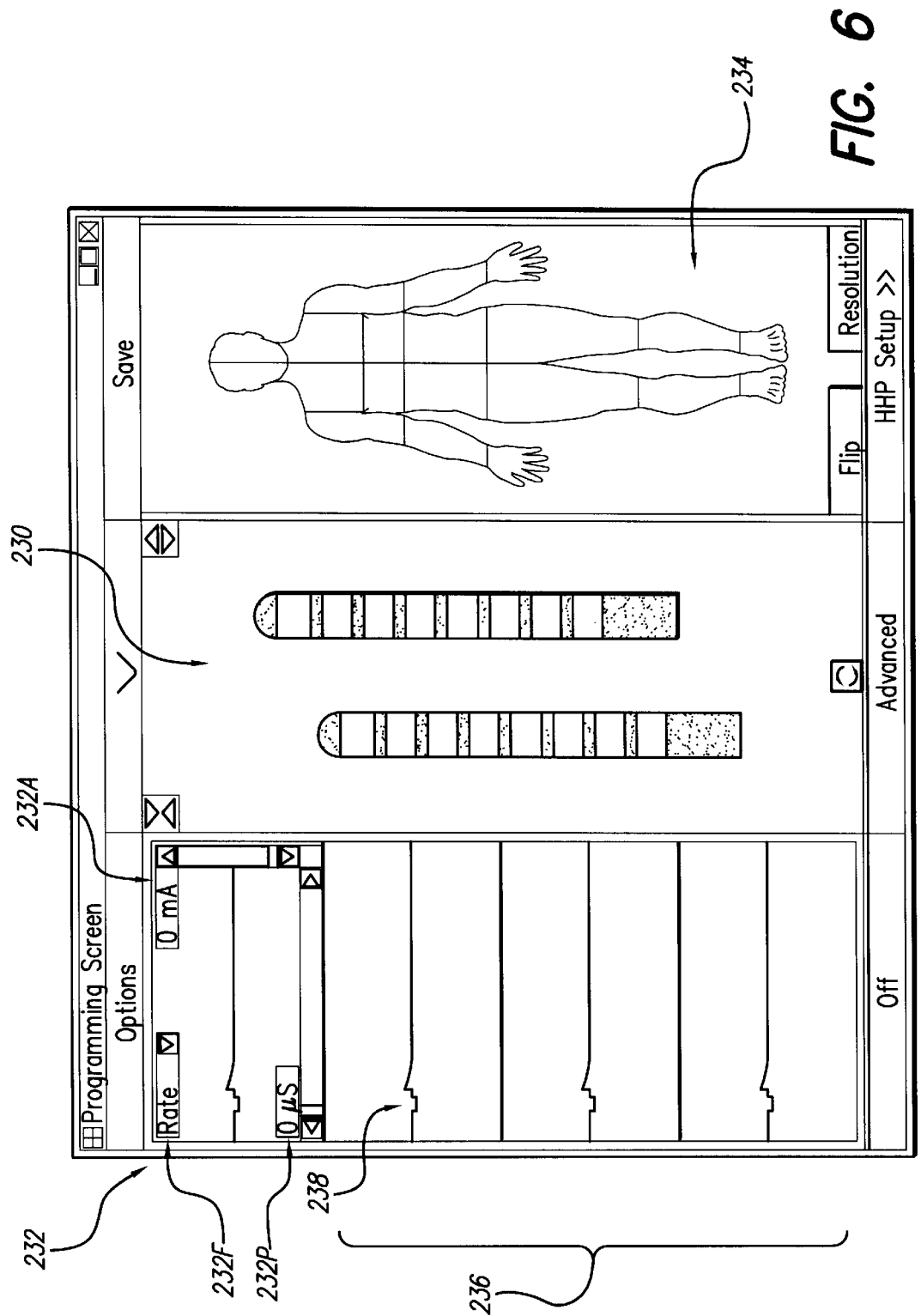
FIG. 6 depicts a representative programming screen that may be used as part of the programming system features of the invention.

A representative programming window is illustrated in FIG. 6. As seen in FIG. 6, included in the display is a representation 230 of the type and orientation of the electrode array(s) that have been selected. Such selection is made from a group of possible electrode choices. Monopolar and bipolar sensitivity (max and min) thresholds are determined for each electrode for the displayed electrode array configuration.

Pain and/or paresthesia mapping is available to identify electrode effects through the threshold testing process. To aid in this process, a human Figure 234 is displayed on the display screen associated with the programming computer. This human Figure 234 is divided into body regions. Such body regions are also referred to, for purposes of the present invention, as "dermatones," "body subdivisions," "body areas," or similar language, as described more fully below in conjunction with the description of FIGS. 7A–7D.

In use, a pain or paresthesia area or region is activated by toggling a color box, e.g., red or blue, that is superimposed over the affected body area. One color, e.g., is used to represent pain; while the other color, e.g, blue, is used to represent paresthesia. As the cursor is moved over different body segments or regions, such segments change color to the active color and can be locked to the active color by clicking the mouse, or depressing a key or button. The paresthesia color is always transparent (top layered) so that pain segments can be seen through it. Multiple body segments can be selected individually, or as a group at intersections. By clicking on a segment, the active color is toggled off and on without affecting the alternate color. The object is to match or map the paresthesia segments with the pain segments. Such pain/paresthesia mapping feature may advantageously be used with expert algorithms to automate the programming process. Alternatively, the patient and clinician/physician may simply work together and use a trial-and-error procedure in order to best fit the paresthesia segments with the pain segments.

Figure 7A:
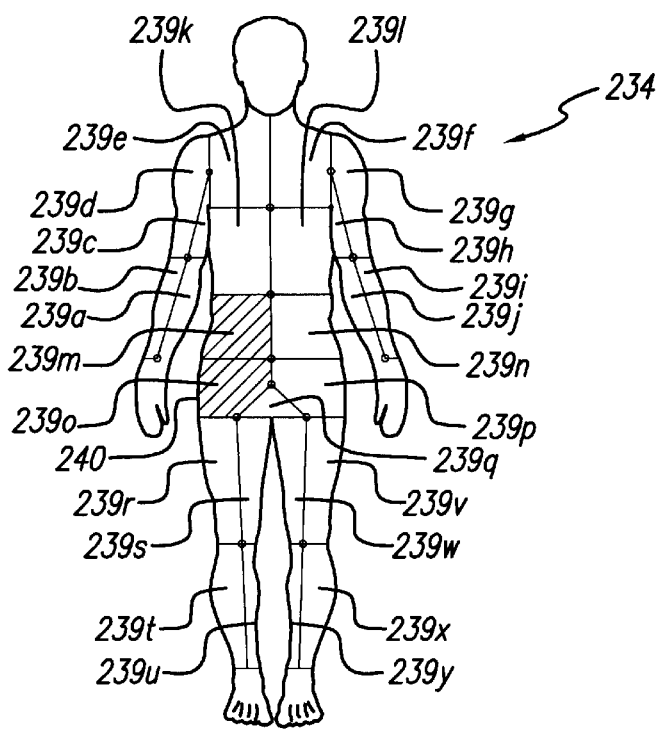
FIGS. 7A, 7B, 7C and 7D show the display of a human body, divided into regions, dermatones, or other subdivisions of the body, which display is presented on the programming screen, and further illustrate an exemplary sequence of selections made by a patient as the invention is used to match a region of pain with a region of paresthesia.

In order to explain in more detail how the pain/paresthesia mapping is performed, reference is next made to FIGS. 7A, 7B, 7C and 7D, where the human Figure 234 displayed on the programming screen is shown in more detail. As seen in FIG. 7A, the human Figure 234 is divided into a multiplicity different regions 239a, 239b, 239c, . . . 239y. For purposes of the present invention, such regions 239a, 239b, . . . 239y may also be referred to as "dermatones," "body subdivisions," "body areas," or similar language. While the human FIG. 234 shown in FIGS. 7A–7D is shown as being divided into twenty-five such regions 239 (239a through 239y), such number of regions is only exemplary.

To perform the pain/paresthesia mapping in accordance with the invention, the patient first identifies a region of pain. By way of example, in FIG. 7A, the patient has identified a region 240 (depicted in FIG. 7A as a right-slanting-hatched area, but preferably depicted on the programming screen in FIG. 6 by a different color, e.g., red) as a region of pain. This pain region 240 comprises the two regions 239m and 239o on the left side of the patient comprising the lower back and pelvic areas. Such pain region 240 may be identified by simply moving the cursor over areas 239m and 239o and clicking a button, e.g., a mouse button or a keyboard button.

Once the patient has identified a pain region 240, the programming computer uses known data regarding the relationships between the electrode physical locations and the body to select a first electrode combination through which a stimulus of selected operating parameters may be applied. Once selected, a stimulus having the selected operating parameters is applied to the selected electrode combinations to test whether the resulting paresthesia is in the same location as the pain region 240. Thus, for example, after feeling or sensing the paresthesia, the patient identifies the location of the paresthesia on the human FIG. 234. By way of example, suppose the patient senses the paresthesia in a paresthesia region which is identified as region 242 in FIG. 7B. (depicted in FIG. 7B as a left-slanting-hatched area, but preferably depicted on the programming screen in FIG. 6 by a different color, e.g., blue). The paresthesia area comprises the individual regions 239m, 239n and 239p, one region of which, 239m, overlaps with a portion of the pain region 240, but the other regions of which, 239n and 239p, do overlap with the pain region 240.

Figure 7B:
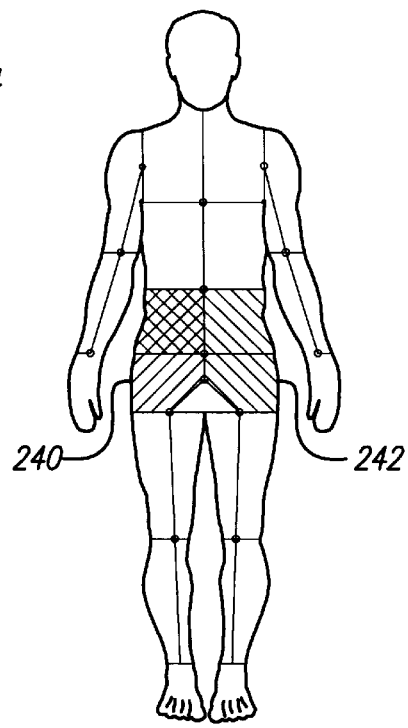
Figure 7C:
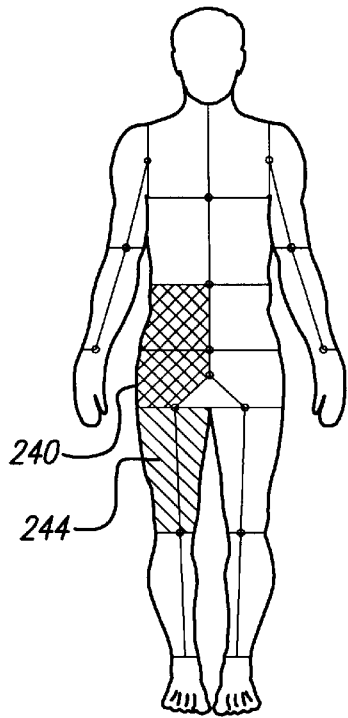
Figure 7D:
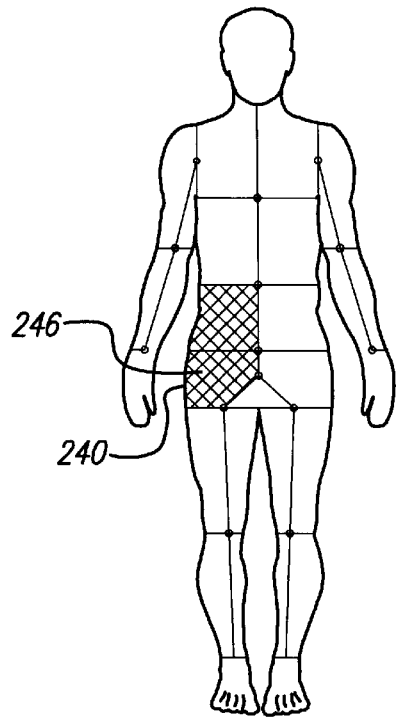

Once the patient has identified the paresthesia region 242, the programming computer uses this information, in combination with other information stored therein, to determine what modifications need to be made to the stimulation parameters or electrode selection in order to steer the paresthesia region 242 (left-slanting-hatched area) over the pain region (right-slanting-hatched area). For example, the newly selected stimulus parameters, including the selected electrode combination, may produce a new paresthesia region 244 that not only moves over the pain region 240 but also extends down into the left leg into regions 239r and 239s, as shown in FIG. 7C. A subsequent iteration, i.e., the selection of a different electrode combination and/or the modification of the stimulus parameters produces a new paresthesia region 246 (left-slanting-hatched area) that matches, or merges with, the pain region 240, as illustrated in FIG. 7D.

Once a match has been obtained between the pain region and the paresthesia region, the programming data, e.g., the operating parameter set, including the selected electrode combination, may be programmed into the memory of the implantable pulse generator so that such data can thereafter be used to control the operation of the IPG, and to further aid in subsequent programming sessions.

Figure 8:
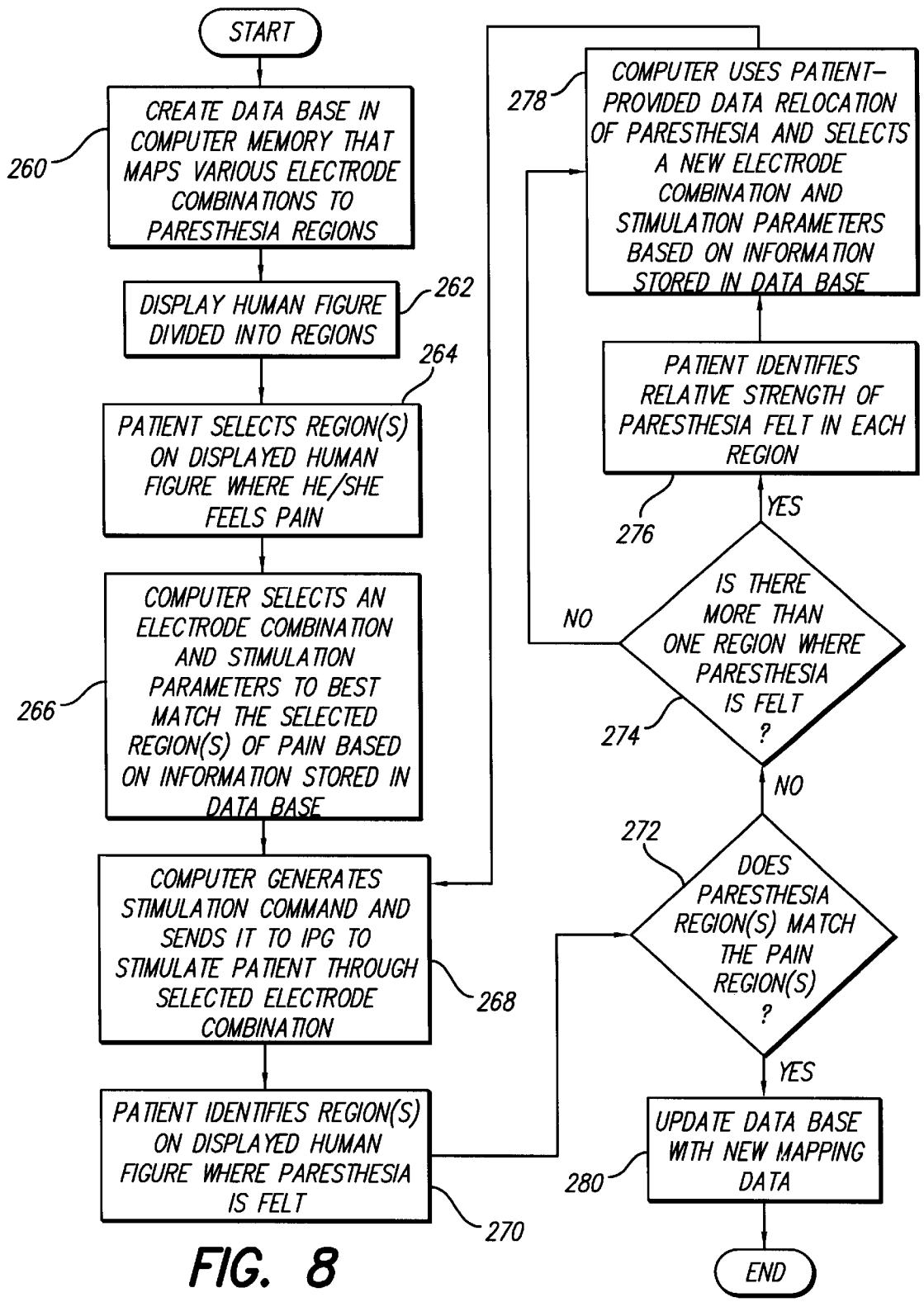
FIG. 8 is a flow chart that depicts the main steps associated with programming an implant device in accordance with the present invention.

The programming approach described above in connection with FIGS. 7A–7D is depicted in flow chart form in FIG. 8. As seen in FIG. 8, a first preliminary step associated with the method (block 260) involves creating a data base and storing such data base in the memory of the programming computer that maps various electrode combinations to paresthesia regions. Such data base may include data relating to known anatomical relationships between the spine and the body, as well as other known medical data.

The method next includes displaying the human figure on a programming screen (block 262 of FIG. 8) divided into regions. The programming software that performs this function of displaying a human figure may be referred to as first program data. The patient then selects those regions (one or more) on the human figure which best represent the locations where he or she feels pain (block 264).

In response to the patient selection which identifies the pain region, the programming computer automatically selects an electrode combination and stimulation parameters which, according to its programming software, would best provide a paresthesia region for the patient that matches the identified pain region (block 266). The data in the data base stored in the computer (block 260) aids in this process. For example, the data in the data base may indicate that if pain is identified in location "X" (which X is any of the regions 239*a*, 239*b*, 239*c*, . . . shown in FIG. 7A), then a stimulus should be provided through electrode "Y", where electrode "Y" is one of the electrodes connected to the IPG. The stimulus parameters may initially be selected as nominal parameters. Selection algorithms, implemented in software or firmware within the computer, may be readily fashioned by those of skill in the art to automatically make this initial selection. The programming software that performs the function of making the initial electrode and stimulus parameter selection may be referred to as second program data.

Still with reference to FIG. 8, once the electrode combination and stimulation parameters have been initially selected, then the programming computer generates the appropriate command signals to cause the implantable pulse generator (IPG) to stimulate the patient through the selected electrode combination (block 268). As a result of such stimulation, the patient senses a region of paresthesia, and is thus able to identify the region of paresthesia on the displayed human figure (block 270). The programming computer, using an appropriate algorithm which may be referred to as third program data, determines the degree of mismatch between the pain region and paresthesia region (block 272). Such matching algorithm, in one form, simply quantifies the amount of overlap between the identified paresthesia region and the selected pain region using the defined regions 239*a*, 239*b*, 239*c*, . . . (see FIG. 7A) on the human figure. Other, more sophisticated matching algorithms, as are known in the art, may also be used for this purpose.

If the degree of mismatch between the paresthesia region and the pain region exceeds a prescribed threshold, e.g., if the mismatch is greater than 80% (or any other selected percentage), i.e., if only 20% of the pain region overlaps with the paresthesia region, then a further iteration of selecting a new electrode combination and/or stimulus parameters, is needed. Such further iteration involves having the programming computer select a new electrode combination and stimulation parameters (block 278). Such selection is made based on the paresthesia region information provided by the patient and other data stored in the data base. For purposes of the invention, such information and data may be referred to as fourth program data. The fourth program data will typically comprise the second program data referred to above, modified in accordance with the paresthesia region information provided by the patient. It is the function of the fourth program data to modify the electrode combination and stimulation parameter selection so as to move the paresthesia region closer to the pain region, so that eventually the two regions merge or overlap.

As shown in FIG. 8, an optional step that may be used with the method shown in FIG. 8, once a determination has been made that the mismatch between the paresthesia region and the pain region exceeds a prescribed threshold (block 272), i.e., that there is not a match between the two regions, is to determine whether the paresthesia region covers more than one region (block 274). That is, a determination is made as to whether the paresthesia region includes more than one of the regions 239 defined in the human figure. For example, as shown in FIG. 7B, the initial paresthesia region 242 includes three defined regions on the human figure, regions 239*m*, 239*n* and 239*p*. In such instance, an option associated with the invention allows the patient to identify the relative strength of the paresthesia in each region (block 276). That is, the patient may indicate whether the paresthesia sensed in human figure region 239*m* is stronger than the paresthesia sensed in human figure regions 239*n* or 239*p*. Such comparative paresthesia strength data is then used by the programming computer, when available, to guide the new selection of electrode combinations and stimulation parameters (block 278).

If the degree of mismatch between the paresthesia region and the pain region is less than a prescribed threshold, e.g., if the mismatch is less than 10% (or any other selected percentage), i.e., if 90% of the pain region overlaps with the paresthesia region, then a match condition is assumed (YES branch from block 272). In such instance, the electrode selection and stimulation parameters that resulted in such match condition may be sent to and stored in the IPG, or other implant device, to control the operation of the device in a manner that regularly overlays the paresthesia region on the pain region. With the programming of the implant device, the data base created in the computer memory is preferably updated with the data that produced the match condition. Should the pain region move over time, then the programming process shown in FIG. 8 can be repeated, as required.

Thus, it is seen that the method shown in FIG. 8, or variations thereof, provides a method for use with a programming device linked with an implantable device, such as an implantable spinal cord stimulator, that allows the patient to easily identify a region of pain and then a region of paresthesia, so that the programming device may then automatically change selected stimulation parameters, including selected combinations of electrodes, to cause the region of paresthesia to overlap or merge with the region of pain, thereby alleviating the pain.

Returning to FIG. 6, the programming window screen is also used to program electrode configurations and the desired output parameters for each of the available channels, e.g., each of four channels. To illustrate how this is done, consider area 236 of the screen shown in FIG. 6. All four channels are selectable from this screen. The channels are selected for programming by pointing and clicking using a mouse or other similar pointing/selection device. The default selection is the first channel. Selecting a channel causes the output parameters and electrodes for that channel to be displayed, so that they can be manipulated. Once selected, continual clicking of the channel toggles stimulation between active ON and PAUSED, with a settable soft start. This soft start feature is explained in more detail below. Selection of another channel does not change any of the settings of a previous channel. A channel that has been selected as an active ON channel is represented by stimulation pulses, see area 238. Channels are identified by number, but can also be selectively or automatically named by paresthesia location (i.e., legs, back, left arm, etc.) from mapping functions.

Before electrodes are displayed on the screen for programming, the array type and orientation must be selected. The number of implanted and available electrodes is typically automatically determined by impedance measurements during hardware interrogation. Pointing to the electrode box 230 provides an electrode array selection, based on the number of detected electrodes, with preset visual forms. Once the array configuration is selected, it is displayed on the screen with point and click selectable electrodes. For example, one click may be used to specify a cathode; two clicks to specify an anode; and a third click to specify a neutral (floating or non-connected) electrode. Cathode, anode and neutral selections are indicated by a color change. By clicking an electrode to a cathode or anode state, the electrode is assigned to the active channel. If desired, a representation of current fields created by electrodes of a channel may also be displayed within this representation.

The amplitude, pulse width and rate are adjustable by mouse or arrow keys for the selected channel, using e.g., the "channel settings" area 232 of the programming screen. In one embodiment, amplitude, on this main programming screen, is programmable by channel, and applied as a distribution between maximum and sense thresholds for channel assigned electrodes. The amplitude for the channel is selected as a level from 1 through 10 where a "1" represents the sense threshold for each electrode in the channel, and a "10" represents the maximum threshold, as described in the previously-referenced patent application Ser. No. 60/172,167, now U.S. Pat. No. 6,381,496 B1. The actual magnitude or amplitude of the current, in mA, may be displayed, as shown in FIG. 6, or may not be displayed. The pulse width and rate are also selectable for the channel, and applied to the channel-assigned electrodes.

Although the programming software permits a physician to program electrodes by channel, each electrode is individually controlled by the implant, and telemetered data is electrode specific. When a channel is programmed to stimulation rates over 150 pps, the number of additional channels may be limited (due to battery capacity). A toggle lock/unlock button for each parameter allows the programming physician to set which parameters are available within the patient hand-held programmer 202 (FIG. 1).

The settings for up to four channels are referred to as a "program."Selectable default parameter settings may thus comprise a program. A store/apply button records all the settings with a program number. In a preferred embodiment, up to twenty programs can be named, stored and selected form a drop-down program list. Thus, programs may be sequentially or selectively tried by the patient so that the patient may compare how one "program" feels compared to another.

The advanced programming window generally allows the output parameters for each channel to be programmed with additional capability and specificity. For example, biphasic verses passive balance pulses, active multipolar driving of cathodes and anodes (field focusing), and amplitude selection for individual electrodes.

Unique programming algorithms may also be employed which provide, e.g., automated and directional programming features. Automated programming may be used, e.g., to use known thresholds and pain/paresthesia mapping to recommend configurations and parameters based on preset rules and database information. Automated programming advantageously maps paresthesia sites over pain sites. Directional programming features may be as disclosed, e.g., in U.S. Pat. No. 6,052,624, previously referenced. Such directional programming uses a joystick, or other means, to configure electrodes within certain limitations for selection, polarity, and amplitude distribution in response to a directional input and in an intuitive and physiologic manner.

Advantageously, the programming software used within the clinician programmer 204 (FIG. 1), also referred to herein as the programming computer, may run under conventional operating systems commonly used within personal computers (PCs). The preferred clinician programmer is a Pentium-based PC, operating at 100 MHz or more, with at least 32 Mbytes of RAM. Examples of an operating system for use in such a system include Windows 95/98/00 or Windows NT 4.0. Such programming software also supports multiple languages, e.g., English, French. German, Spanish, Japanese, etc.

As described above, it is thus seen that the present invention provides a programming device or apparatus for use with an implantable stimulator, such as an implantable spinal cord stimulator. Advantageously, the programming device allows the patient to easily identify a region of pain and then a region of paresthesia. The programming device then uses this information to automatically change the selected stimulation parameters, including the selected combinations of electrodes, to cause the region of paresthesia to overlap or merge with the region of pain, thereby alleviating the pain.

While the invention herein disclosed has been described by means of specific embodiments and applications thereof, numerous modifications and variations could be made thereto by those skilled in the art without departing from the scope of the invention set forth in the claims.

What is claimed is:

1. A method of programming an implant device, the implant device comprising an implantable pulse generator having an implantable electrode array connected thereto, the implantable pulse generator having electrical circuitry therein that generates electrical stimulation pulses in accordance with programming data, which electrical stimulation pulses are delivered to body tissue of a patient through a selected combination of a multiplicity of electrodes on the electrode array, wherein the programming method comprises:

(a) creating a data base that maps various electrode combinations to paresthesia regions of the body;

(b) storing the data base in a programming computer;

(c) displaying a human figure on a screen of the programming computer, and dividing the human figure into a multiplicity of regions;

(d) selecting at least one region on the displayed human figure where the patient feels pain;

(e) selecting a combination of electrodes and stimulation parameters adapted to produce paresthesia in the same at least one region of pain;

(f) generating stimulation pulses and delivering the stimulation pulses to the selected combination of electrodes through the implantable pulse generator;

(g) identifying at least one region of paresthesia on the displayed human figure where the stimulation pulses generated in step (f) produce paresthesia;

(h) determining the degree of mismatch between the at least one region of paresthesia identified in step (f) and the at least one region of pain selected in step (d);

(i) if the degree of mismatch exceeds a prescribed level, selecting a new combination of electrodes and stimulation parameters including stimulus amplitude and pulsewidth for each independently programmable electrode, in order to steer a stimulus current field, which selecting of electrodes and parameters is based on the identified at least one region of paresthesia and the degree of mismatch, and repeating steps (f), (g) and (h); and (j) if the degree of mismatch is less than the prescribed level, programming the implantable pulse generator with the programming data that produces the least mismatch.

2. The method of programming set forth in claim 1 wherein steps (c), (e), (f), (h), (i) and (j) are carried out automatically by the programming computer as controlled by an operating program and program data stored in the computer.

3. The method of programming set forth in claim 2 wherein steps (d) and (g) are performed by selecting regions on the displayed human figure by manually moving a computer-generated marker over the region to be selected.

4. The method of programming set forth in claim 3 wherein moving the computer marker is accomplished by at least one of the following: pressing a key, moving a mouse, moving a track ball, moving a finger over a touch-sensitive screen, moving a light beam, or speaking voice commands.

5. The method of programming set forth in claim 3 wherein step (g) further comprises quantifying the degree of paresthesia that is felt in the identified region of the displayed human figure.

6. A system for programming an implantable pulse generator having an implantable electrode array connected thereto, and wherein the implantable pulse generator has electrical circuitry therein that generates electrical stimulation pulses in accordance with programming data, which electrical stimulation pulses are delivered to body tissue of a patient through a selected combination of a multiplicity of electrodes on the electrode array, wherein the system for programming comprises:

a programming computer linked to the implantable pulse generator, the programming computer having a display screen, and means for generating a cursor on the screen that may be manually moved about the screen by a user;

means for displaying a human figure on a screen of the programming computer, the human figure being divided into a multiplicity of regions;

means for selecting at least one region on the displayed human figure where the patient feels pain;

means for selecting a combination of electrodes and stimulation parameters adapted to produce paresthesia in the same at least one region of pain;

means for generating stimulation pulses and delivering the stimulation pulses to the selected combination of electrodes through the implantable pulse generator;

means for identifying at least one region of paresthesia on the displayed human figure where the generated stimulation pulses produce paresthesia;

means for determining the degree of mismatch between the identified at least one region of paresthesia and the selected at least one region of pain;

means for selecting a new combination of independently programmable electrodes and stimulation parameters, including stimulus amplitude and pulsewidth, in order to steer a stimulus current field based on the identified at least one region of paresthesia and the degree of mismatch if the degree of mismatch exceeds a prescribed level and determining a new degree of mismatch with the newly selected combination of electrodes and stimulation parameters, whereby the degree of mismatch may be minimized; and means for programming the implantable pulse generator with the programming data that produces the least mismatch.

7. The system of claim 6 wherein the human figure displayed on the displayed screen is divided into at least 25 regions.

8. The system of claim 6 wherein the means for selecting at least one region on the displayed human figure where the patient feels pain comprises means for marking the regions of pain with a first color.

9. The system of claim 8 wherein the means for identifying at least one region on the displayed human figure where the generated stimulation pulses produce paresthesia comprises means for marking the paresthesia regions with a second color, wherein the second color is transparent so that the presence of the first color may be seen therethrough.

10. Programming system for programming an implantable pulse generator, wherein the implantable pulse generator comprises electrical circuitry that generates electrical stimulation pulses in accordance with programming data, and an electrode array having a multiplicity of electrodes coupled to the electrical circuitry, each electrode independently programmable for amplitude and pulsewidth, the system comprising:

a programming computer linked to the implantable pulse generator, the programming computer having a display screen, and means for generating a cursor on the display screen that may be manually moved anywhere on the screen by a user;

first program data stored in the programming computer that causes a human figure to be displayed on the display screen of the programming computer, wherein the human figure is divided into a multiplicity of regions;

means for marking at least one region on the displayed human figure to represent a location whereat the patient feels pain;

second program data stored in the programming computer that causes a combination of electrodes and stimulation parameters to be selected that are adapted to produce paresthesia in the same general location where the patient feels pain;

means for marking at least one region on the displayed human figure to represent a location whereat the patent feels paresthesia;

third program data stored in the programming computer that determines the degree of mismatch between the location where the patient feels pain and the location where the patient feels paresthesia as a result of stimulation pulses produced by the second program data;

fourth program data stored in the programming computer that selects a combination of independently programmable electrodes and new stimulation parameters for each selected electrode to directionally steer the stimulus current in order to minimize the degree of mismatch between the location where the patient feels pain and the location where the patient feels paresthesia as a result of recently applied stimulation pulses; and fifth program data stored in the programming computer that causes the combination of electrodes and stimulation parameters that minimize the degree of mismatch to be included in programming data that thereafter controls the operation of the implantable pulse generator.

11. The programming apparatus of claim 10 wherein the human figure displayed on the display screen is divided into at least twenty-five regions.

12. The programming apparatus of claim 10 wherein the programming computer comprises a lap top computer having a display screen.

13. The programming apparatus of claim 10 wherein the means for marking at least one of the multiplicity of regions on the human figure whereat the patient feels pain includes: a pressable key, a movable mouse, a movable track ball, a touch-sensitive screen, a light-beam sensitive screen, or means for recognizing spoken voice commands.

14. The programming apparatus of claim 13 wherein the means for marking further includes means for displaying marked regions of the displayed human figure where the patient feels pain with a first display characteristic.

15. The programming apparatus of claim 14 wherein the first display characteristic comprises a first color.

16. The programming apparatus of claim 15 wherein the first color comprises red.

17. The programming apparatus of claim 10 wherein the means for marking at least one of the multiplicity of regions on the human figure whereat the patient feels paresthesia includes: a pressable key, a movable mouse, a movable track ball, a touch sensitive screen, a light-beam sensitive screen, or means for recognizing spoken voice commands.

18. The programming apparatus of claim 17 wherein the means for marking further includes means for displaying marked regions of the displayed human figure where the patient feels paresthesia with a second display characteristic that is transparent relative to the first display characteristic, wherein the presence of the first display characteristic may be seen through the second display characteristic.

19. The programming apparatus of claim 18 wherein the second display characteristic comprises a second color different from the first color.

20. The programming apparatus of claim 19 wherein the second color comprises green or blue.

* * * * *